(12) United States Patent
Clark et al.

(10) Patent No.: US 8,395,006 B2
(45) Date of Patent: Mar. 12, 2013

(54) PROCESS FOR MAKING HIGH OCTANE GASOLINE WITH REDUCED BENZENE CONTENT BY BENZENE ALKYLATION AT HIGH BENZENE CONVERSION

(75) Inventors: Michael C. Clark, Chantilly, VA (US); Benjamin S. Umansky, Fairfax, VA (US); Elizabeth A. Nye, Houston, TX (US); Mark J. Reichensperger, Billings, MT (US); William C. Lewis, Vienna, VA (US)

(73) Assignee: ExxonMobil Research and Engineering Company, Annandale, NJ (US)

( * ) Notice: Subject to any disclaimer, the term of this patent is extended or adjusted under 35 U.S.C. 154(b) by 191 days.

(21) Appl. No.: 12/720,345

(22) Filed: Mar. 9, 2010

(65) Prior Publication Data

US 2010/0300930 A1 Dec. 2, 2010

Related U.S. Application Data

(60) Provisional application No. 61/209,995, filed on Mar. 13, 2009.

(51) Int. Cl.
*C07C 2/64* (2006.01)

(52) U.S. Cl. ........................ 585/447; 585/446

(58) Field of Classification Search ................... None
See application file for complete search history.

(56) References Cited

U.S. PATENT DOCUMENTS

| | | | |
|---|---|---|---|
| 2,381,175 A | 8/1945 | Mattox | |
| 3,751,504 A | 8/1973 | Keown | |
| 4,016,218 A | 4/1977 | Haag et al. | |
| 4,153,638 A | 5/1979 | Bercik et al. | |
| 4,169,111 A | 9/1979 | Wight | |
| 4,439,405 A | 3/1984 | Bailey et al. | |
| 4,459,426 A | 7/1984 | Inwood et al. | |
| 4,463,211 A | 7/1984 | Manning | |
| 4,471,147 A | 9/1984 | Owen et al. | |
| 4,547,605 A | 10/1985 | Kresge et al. | |
| 4,579,990 A | 4/1986 | Keyworth | |
| 4,746,762 A | 5/1988 | Avidan et al. | |

(Continued)

FOREIGN PATENT DOCUMENTS

| | | |
|---|---|---|
| CN | 1464035 A | 12/2003 |
| EP | 0029302 A1 | 5/1981 |

(Continued)

OTHER PUBLICATIONS

Search Report, PCT/US2010/000731, mailed Mar. 2, 2012.

(Continued)

*Primary Examiner* — Tam M Nguyen
(74) *Attorney, Agent, or Firm* — Malcolm D. Keen; Glenn T. Barrett

(57) ABSTRACT

A process for the alkylation of a benzene-containing refinery stream such as reformate with light refinery olefins which is capable of achieving high benzene conversion levels operates in a fixed bed of an MWW zeolite catalyst, preferably MCM-22, in single pass mode in the liquid phase at a relatively low to moderate temperatures with pressure maintained at a value adequate to ensure subcritical operation. High levels of benzene conversion with conversions of at least 90% and higher, e.g. 92% or 95% or even higher are achievable. A high octane product is produced, comprising mono-, di- and tri-alkylbenzenes with lesser levels of the tetra-substituted products. By operating with staged olefin injection, the end point of the alkylation product can be maintained at a low value while, at the same time, achieving high levels of benzene and olefin conversion.

25 Claims, 10 Drawing Sheets

U.S. PATENT DOCUMENTS

| | | | |
|---|---|---|---|
| 4,826,667 A | 5/1989 | Zones et al. | |
| 4,827,069 A | 5/1989 | Kushnerick et al. | |
| 4,891,458 A | 1/1990 | Innes et al. | |
| 4,950,387 A | 8/1990 | Harandi et al. | |
| 4,950,823 A | 8/1990 | Harandi et al. | |
| 4,954,325 A | 9/1990 | Rubin et al. | |
| 4,956,514 A | 9/1990 | Chu | |
| 4,962,256 A | 10/1990 | Le et al. | |
| 4,975,179 A | 12/1990 | Harandi et al. | |
| 4,992,606 A | 2/1991 | Kushnerick et al. | |
| 4,992,607 A | 2/1991 | Harandi et al. | |
| 5,003,119 A | 3/1991 | Sardina et al. | |
| 5,073,653 A | 12/1991 | Butler | |
| 5,077,445 A | 12/1991 | Le | |
| 5,175,185 A | 12/1992 | Chandraratna | |
| 5,185,486 A | 2/1993 | Collin et al. | |
| 5,236,575 A | 8/1993 | Bennett et al. | |
| 5,250,277 A | 10/1993 | Kresge et al. | |
| 5,334,795 A | 8/1994 | Chu et al. | |
| 5,336,820 A | 8/1994 | Owen et al. | |
| 5,362,697 A | 11/1994 | Fung et al. | |
| 5,371,310 A | 12/1994 | Bennett et al. | |
| 5,414,172 A | 5/1995 | Chin et al. | |
| 5,434,326 A | 7/1995 | Gajda et al. | |
| 5,491,270 A | 2/1996 | Chin et al. | |
| 5,493,065 A | 2/1996 | Cheng et al. | |
| 5,545,788 A | 8/1996 | Cheng et al. | |
| 5,865,986 A | 2/1999 | Buchanan et al. | |
| 5,877,370 A | 3/1999 | Gajda | |
| 5,900,520 A | 5/1999 | Mazzone et al. | |
| 5,902,917 A | 5/1999 | Collins et al. | |
| 5,907,073 A | 5/1999 | Ghosh | |
| 6,025,534 A | 2/2000 | Valente et al. | |
| 6,043,402 A | 3/2000 | Gajda | |
| 6,051,521 A | 4/2000 | Cheng et al. | |
| 6,060,632 A | 5/2000 | Takamatsu et al. | |
| 6,077,498 A | 6/2000 | Diaz Cabanas et al. | |
| 6,281,399 B1 * | 8/2001 | Schulz et al. | 585/323 |
| 6,284,398 B1 | 9/2001 | Kiryu | |
| 6,339,179 B1 * | 1/2002 | Schulz et al. | 585/323 |
| 6,479,721 B1 | 11/2002 | Gajda et al. | |
| 6,500,999 B2 | 12/2002 | Di Girolamo et al. | |
| 6,512,153 B1 * | 1/2003 | Cappellazzo et al. | 585/467 |
| 6,525,234 B1 | 2/2003 | Dandekar et al. | |
| 6,703,356 B1 | 3/2004 | Wu | |
| 6,756,030 B1 | 6/2004 | Rohde et al. | |
| 6,809,228 B2 | 10/2004 | Ducreux et al. | |
| 6,855,855 B2 | 2/2005 | Van Den Brink et al. | |
| 6,872,864 B2 | 3/2005 | Gajda et al. | |
| 6,911,568 B1 * | 6/2005 | Dandekar et al. | 585/467 |
| 6,977,319 B2 | 12/2005 | Campbell et al. | |
| 7,091,390 B2 | 8/2006 | Jan et al. | |
| 7,498,474 B2 * | 3/2009 | Umansky et al. | 585/449 |
| 7,525,002 B2 * | 4/2009 | Umansky et al. | 585/323 |
| 2002/0121459 A1 | 9/2002 | Pradhan et al. | |
| 2002/0175107 A1 | 11/2002 | Huff et al. | |
| 2004/0171899 A1 | 9/2004 | Pohl | |
| 2004/0181106 A1 | 9/2004 | Nurminen et al. | |
| 2004/0198586 A1 | 10/2004 | Mohr et al. | |
| 2004/0242404 A1 | 12/2004 | Hwang et al. | |
| 2006/0135832 A1 | 6/2006 | Vora et al. | |
| 2006/0194998 A1 | 8/2006 | Umansky et al. | |
| 2008/0194890 A1 | 8/2008 | Brown | |

FOREIGN PATENT DOCUMENTS

| | | |
|---|---|---|
| WO | 9316020 A2 | 8/1993 |
| WO | 9717290 A1 | 5/1997 |
| WO | 0127053 A1 | 4/2001 |
| WO | 0183408 A1 | 11/2001 |
| WO | 0196013 A1 | 12/2001 |
| WO | 02060191 A2 | 8/2002 |
| WO | 03076074 A1 | 9/2003 |
| WO | 2004085062 A1 | 10/2004 |
| WO | 2008088934 A1 | 7/2008 |

OTHER PUBLICATIONS

Written Opinion, PCT/US2010/000731, mailed Mar. 2, 2012.
R.J. Hengstebeck, Petroleum Processing Principles and Applications, (1959), pp. 212-218, New York, McGraw-Hill Book Company, Library Congress Cat. No. 58-13006.

* cited by examiner

US 8,395,006 B2

PROCESS FOR MAKING HIGH OCTANE GASOLINE WITH REDUCED BENZENE CONTENT BY BENZENE ALKYLATION AT HIGH BENZENE CONVERSION

CROSS REFERENCE TO RELATED APPLICATIONS

This application relates to and claims priority to U.S. Provisional Patent Application No. 61/209,995, filed on Mar. 13, 2009.

This application is related to U.S. published patent applications: US 2006/0194998, now abandoned, US 2006/0194996, now U.S. Pat. No. 7,476,774 and US 2006/0194995, now U.S. Pat. No. 7,525,002 entitled, respectively, "Process For Making High Octane Gasoline With Reduced Benzene Content", "Liquid Phase Aromatics Alkylation Process" and "Gasoline Production by Olefin Polymerization with Aromatics Alkylation".

FIELD OF THE INVENTION

This invention relates to a process for the production of gasoline boiling range motor fuel by the alkylation of benzene.

BACKGROUND OF THE INVENTION

Benzene is a naturally-occurring constituent of crude oil and a constituent of many petroleum products. Its average concentration in motor gasoline in the United States is on the order of 1%. Benzene has received much attention from regulatory agencies because it has been classified as a known human carcinogen (EPA classification, Group A) and causes blood disorders (leukemia) in workers exposed to high concentrations.

With the toxicity factor in view, the US Environmental Protection Agency and regulatory agencies in other countries and regions, specifically, the European Union, have set rules for some time regulating the levels of benzene permitted in motor gasolines. Benzene in conventional gasoline is currently controlled indirectly by regulations that limit benzene via exhaust toxics tied, in most cases, to a refinery's Mobile Source Air Toxics (MSAT) Phase 1 baseline but new regulations proposed by the US Environmental Protection Agency, will subject all US gasoline to benzene restrictions at levels far lower than those currently applicable only to reformulated gasoline (RFG) which constitutes about 30-35% of the US gasoline pool. RFG was held to a benzene limit of less than 1.0 vol % but under MSAT Phase 2, regulations are expected to reduce benzene in all US gasoline to an annual average 0.62 vol % starting in 2011; in addition, refiners must also meet a maximum average benzene standard of 1.3 vol % beginning in 2012. The current limit on benzene in regions subject to the Euro III and Euro IV standards is 1 vol %. In addition, all Canadian and Japanese gasoline is subject to the 1.0 vol % limit. Reduction of the benzene content in all US gasoline to 0.6 vol % under EPA MSAT Phase 2 will make it more difficult for foreign suppliers to provide gasoline for the US market. Imported gasoline has supplied more than 10% of US summer gasoline in the past few years and has helped significantly to stabilize US gasoline supplies during periods of high demand. The effect of MSAT Phase 2 on U.S. refiners is, of course, more direct and it is likely that benzene reduction solutions that worked with RFG may be insufficient to meet the new specifications.

For most refiners, benzene reduction will be a compliance issue. A refiner must choose and implement a solution that provides the best value in the highly competitive gasoline market. Solutions will be refinery-specific and determined by the current refinery configuration, the type of reforming unit, the amount of benzene contributed from other blendstocks, amount of oxygenate blended, and access to markets that allow trading of intermediate streams, e.g. benzene to petrochemical plants. A refiner's first step in meeting the new benzene requirement will be to review the benzene contributions to the pool from each source. Next, the operating windows and roles for the existing assets in light of the new regulations will require consideration, factoring in the effects from alternative crudes that may be processed, future refinery expansions, and any changes in FCC unit operations that affect benzene. Once these preliminary steps are complete, the refiner must evaluate all the possible solutions and determine if one offers better economics and flexibility than another.

While removal of benzene from aromatic gasoline blend stocks be required, removal from reformate streams is likely to become the more important factor under the new regulatory regime since a limit of 1 vol % in the gasoline pool, as under current regulations, enables the level of benzene in FCC naphtha, which is about 0.5-1.3 vol % depending on FCC operation, catalyst, and feed, to be given less weight. At a maximum 0.6 vol % benzene in the gasoline pool, however, the contribution from FCC naphtha may require refiners to look at more expensive benzene-reduction solutions. Coupled with this is the need to maximize the size of the gasoline pool, which inevitably requires a higher level of conversion, much of which is provided by the FCC unit.

The main source of benzene in most gasolines is reformate and most current benzene reduction solutions focus on preventing benzene formation in the reforming unit by removing benzene precursors from the reforming unit feed. This solution, however, has the potential drawback of reducing the amount of hydrogen produced in the reformer and so, of reducing the amount of hydrogen produced for other refinery processes such as desulfurization, hydrocracking, FCC feed hydrotreating which themselves can contribute to the quality not only of the refinery gasoline pool but also to the quality of other products and to the cleanliness of the environment.

Extraction of benzene from the reformate, either for petrochemical production or for chemical conversion followed by return of the remainder to the gasoline pool provides a net hydrogen balance of zero but in this case, the volume of the refinery gasoline pool is reduced by the removal of the benzene. The removal of benzene by extraction may also result in a decrease in product octane quality since benzene and other single ring aromatics make a positive contribution to product octane (MON Blending Numbers are 91 for benzene, 112 for toluene, 124 for m-xylene, 124 for isopropylbenzene and 129 for propylbenzene). The retention of aromatics, although not in the form of benzene but rather the less toxic alkylaromatics, is therefore desirable from the viewpoint of good product quality, engine operation and, in addition, the improved fuel economy resulting from the higher volumetric energy content of the aromatics.

Certain processes have been proposed for converting the benzene in aromatics-containing refinery streams to the less toxic alkylaromatics such as toluene and ethyl benzene which in themselves are desirable as high octane blend components. One process of this type was the Mobil Benzene Reduction (MBR) Process which, like the closely related MOG Process, used a fluidized zeolite catalyst in a riser reactor to alkylate benzene in reformate to from alkylaromatics such as toluene.

The MBR and MOG processes are described in U.S. Pat. Nos. 4,827,069; 4,950,387; 4,992,607 and 4,746,762. The fluid bed MBR Process uses a shape selective, metallosilicate catalyst, preferably ZSM-5, to convert benzene to alkylaromatics using olefins from sources such as FCC or coker fuel gas, excess LPG or light FCC naphtha. Normally, the MBR Process has relied upon light olefin as alkylating agent for benzene to produce alkylaromatics, principally in the $C_7$-$C_8$ range. Benzene is converted, and light olefin is also upgraded to gasoline concurrent with an increase in octane value. Conversion of light FCC naphtha olefins also leads to substantial reduction of gasoline olefin content and vapor pressure as well as a decrease in MON sensitivity.

Like the MOG Process, however, the fluid bed MBR Process required considerable capital expenditure, a factor which did not favor its widespread application in times of tight refining margins. The MBR process also used higher temperatures and $C_5$+ yields and octane ratings could in certain cases be deleteriously affected, another factor which has not favored widespread utilization. Other refinery processes have also been proposed to deal with the problems of excess refinery olefins and gasoline; processes of this kind have often functioned by the alkylation of benzene with olefins or other alkylating agents such as methanol. Exemplary processes of this kind are described in U.S. Pat. Nos. 4,950,823; 4,975,179; 5,414,172; 5,545,788; 5,336,820; 5,491,270 and 5,865,986.

Co-pending applications published as US 2006/0194998, US 2006/0194996 and US 2004/0194995, disclosed a simple, economical, fixed bed process for converting benzene to alkylaromatics with light refinery olefins especially ethylene, propylene and butene. The process was notable for its ability to: upgrade $C_2$ and $C_3$ olefin from fuel gas to high octane blending gasoline; increase flexibility in refinery operation to control benzene content in the gasoline blending pool; avoid octane loss and hydrogen consumption associated with alternative reformer feed tailoring and benzene saturation technologies; remove benzene from the refinery gasoline pool without diverting the benzene to other uses; and allow refineries with benzene problems to feed the $C_6$ components (low blending octane values) to the reformer, increasing both the hydrogen production from the reformer while retaining the octane contribution from the high octane alkylaromatics. In operation, an increase of 1-10 numbers of (R+M)/2 may be achieved, depending on the feed composition, benzene conversion and endpoint specification.

Because the main objective of the process is to reduce the benzene content of the feed stream, achieving a high level of benzene conversion is important; complete or near complete conversion of the benzene is an obvious goal. This objective has, however, proved difficult to achieve in view of competing and conflicting process and equipment requirements.

The benzene conversion in the reformate alkylation process needs to achieve a high level in order to meet the gasoline composition specifications. Desirably, the conversion should be at least 90%, preferably at least 95% or even higher in order to maximize the extent of benzene removal. At the same time, the product should be held to meet refinery gasoline pool blending specifications, most notably the end point or T90 specifications which, in the United States, should not exceed 225° C. (437° F.) on the end point and 185° C. (about 365° F.) for T90 (T90 values in this specification in accordance with ASTM D 86). To comply with more restrictive specification such as CARB (California Air Resources Board), a lower figure closer to 145° C. (about 293° F.) will be required for T90. What this means in terms of process design is that highly polyalkylated benzenes are undesirable because of their effect on T90 and, possibly for their other adverse effects in the gasoline pool: 1,3,5 tri-isopropyl benzene and 1,2,4,5-tetraisopropylbenzene each have, for example, a melting point of 118° C. and excessive amounts in the product can lead to crystallization in cold weather. Thus, a balance needs to be struck between the octane boost resulting from alkylation and the resulting increase in melting point and boiling point. Allied to this is also the desirability of conserving refinery olefins which may have other uses if available and of minimizing hydrogen consumption.

SUMMARY OF THE INVENTION

We have now devised a process for the alkylation of a light benzene-containing refinery streams such as reformate, FCC naphtha, virgin light naphtha and steam cracker naphtha, with light refinery olefins which is capable of achieving high benzene conversion levels while producing a product which has a high octane rating and a favorable boiling range without excessive production of heavy ends or undesirable increase in RVP. In addition, an expansion of product volume occurs with its favorable effect on the gasoline pool. Also, since the process provides a route for converting reformer benzene, the proportion of benzene precursors in reformer feeds can be increased so that the production of hydrogen from the reforming operation can be maintained.

According to the present invention, the alkylation process is carried out using a light refinery olefin stream to alkylate a benzene-containing aromatic stream; a combination of process conditions is selected to result in high levels of benzene conversion. The process is operated with a minimum benzene conversion of 60% and in most cases, the minimum will be higher at 70% or 80% or more. Typically, benzene conversion will be held at 90% or higher, with conversion at these levels being achievable readily while still controlling product boiling range parameters. The aromatic feed stream is normally a benzene-rich reformate but other light (D 86 end point less than 200° C. (about 390° F.) aromatic streams, typically with lower benzene contents may be effectively utilized in the process, for example, aromatic virgin naphthas, FCC naphthas and steam cracked naphthas. Typically, the benzene content of the aromatic stream will be at least 5 wt. pct and in most cases 15-40% with the balance of aromatics being toluene and isomeric xylenes which are also subject to alkylation by the olefin co-feed. The preferred olefin feed stream is one which comprises mainly propylene but ethylene and some butylenes may also be present along with light paraffins such as propane, butane and pentane; the presence of the light alkanes is desirable since they act as a heat sink for the exothermic alkylation reaction and accordingly, help to prevent hot spots arising in the catalyst bed. The presence of the paraffins may also result in a boost in product octane and for this reason, the use of refinery grade propylene streams is not only possible but favorable.

The process is operated in a fixed catalyst bed in single pass mode, that is, without recycle of the aromatic stream; the olefin stream is essentially consumed in the reaction. The catalyst is a zeolite-based catalyst of the MWW family, preferably a catalyst based on zeolite MCM-22 or MCM-49. The MWW family of zeolites has shown itself to exhibit high activity and high selectivity together with a long catalyst life under typical operating conditions. Liquid phase, downflow operation is preferred and the process may be operated adiabatically or in isothermal mode. The process is capable of operation at low to medium pressures with no compressor needed. In view of the benign nature of the catalyst and the moderate conditions, carbon steel equipment can be used with no highly stringent metallurgical requirements.

During the alkylation, the aromatic stream is maintained in the liquid phase with the pressure maintained at a value high enough to ensure subcritical operation, typically at values above about 4000 kPag (about 580 psig) although pressures as low as about 2500 kPag (about 360 psig) may be operable depending on the feedstream composition and the temperature. Minimum temperatures are generally in the range of 175-200° C. (347-392° F.), more usually at least 220° C. (428° F.); the maximum will not normally exceed 300° C. (572° F.) with a maximum of 250° C. (482° F.) being normally preferred. Control of the exotherm is assisted by the staged injection of the olefin which also promotes higher benzene conversion together with a reduction of product endpoint (by about 25° C.) and a reduction in the volume of product with end point above the mogas range; a reduction of approximately 50% in the volume of product boiling above the mogas endpoint specification is achievable. Selectivity and catalyst life are also beneficially affected by staged olefin injection.

DRAWINGS

DETAILED DESCRIPTION

Figure 1:
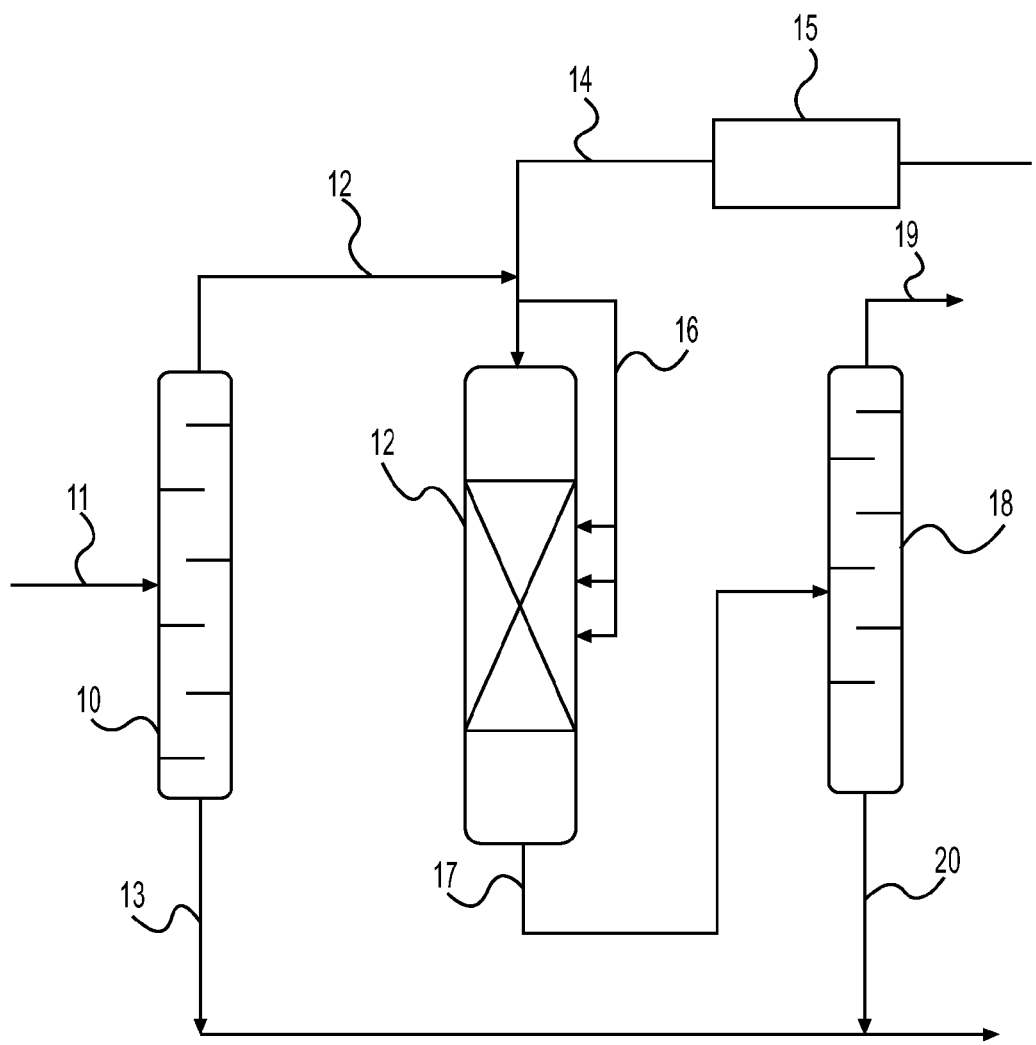
FIG. 1 is a simplified schematic diagram of a process unit for carrying reformate alkylation.

The present aromatics alkylation process uses two essential feedstreams, an aromatic feedstream containing benzene and an light olefin feedstream which is used to alkylate the aromatic feedstream under carefully selected conditions to produce an alkylaromatic product comprising single ring alkylaromatics with up to six substituent alkyl groups, preferably isopropyl groups from propylene as the olefin reactant.
Process Configuration FIG. 1 is a much simplified schematic of a process unit suitable for carrying out the present reformate alkylation process. The feed from the reformer enters splitter 10 through line 11 and is fractionated into a lighter, benzene-enriched concentrate passing out through line 12 and a heavier fraction leaving through line 13. The reformate cut in line 13 enters alkylation reactor 12 together with a light olefin stream coming by way of line 14 from pre-treatment unit 15. Conventional types of pretreatment are suitably applied, including washing, drying, particulate removal etc or other measures calculated to ensure a feed of the appropriate level of purity. Line 14 has branch line 16 which feeds the olefin to multiple injections points along the length of reactor 12. The reactor effluent passes from reactor 12 through line 17 to product fractionator 18 from which light ends exit through overhead 19; the heavier products including the alkylbenzenes formed by alkylation of the benzene with the olefin leave as bottoms through line 20 and can be combined with the heavy ends from splitter 10 in line 13 to be sent to the gasoline pool.
Aromatic Feed The light aromatics stream is almost always a reformer effluent which may be either the whole reformate or a reformate fraction although other sources of aromatic, benzene-rich feeds including light aromatic virgin naphthas, light FCC naphthas, steam cracked naphthas, coker naphthas or pyrolysis gasolines may also be used even though they will normally be less significant for normal refinery operation. Boiling ranges for these feeds will typically be from 50 to 200° C. (about 120 to 390° F.). The aromatic stream may contain other single ring aromatic compounds including alkylaromatics such as toluene, ethylbenzene, propylbenzene (cumene) and the xylenes. In refineries with associated petrochemical capability, these alkylaromatics will normally be removed for higher value use as chemicals or, alternatively, may be sold separately for such uses. Since they are already considered less toxic than benzene, there is no environmental requirement for their inclusion in the aromatic feed stream but, equally, there is no prejudice against their presence unless conditions lead to the generation of more highly substituted alkylaromatics which fall outside the gasoline range or which are otherwise undesirable in gasoline.

The amount of benzene in the aromatics stream is governed mainly by its source and processing history but in most cases will typically contain at least about 5 vol. % benzene, although a minimum of 12 vol. % is more typical, more specifically about 20 or 25 vol. % to 60 vol. % benzene. Normally, the main source of this stream will be a stream from the reformer which is a ready source of light aromatics; in view of the major benzene contribution made by reformates, the process will be described with particular reference to its use with reformate streams although use with other light aromatic streams is also possible. Reformate streams may be full range reformates, light cut reformates, heavy reformates or heart cut reformates. These fractions typically contain smaller amounts of lighter hydrocarbons, typically less than about 10% $C_5$ and lower hydrocarbons and small amounts of heavier hydrocarbons, typically less than about 15% $C_7+$ hydrocarbons. These reformate feeds usually contain very low amounts of sulfur as, usually, they have been subjected to desulfurization prior to reforming so that the resulting gasoline product formed in the present process contains an acceptably low level of sulfur for compliance with current sulfur specifications. Aromatic streams from other source, e.g. virgin and FCC naphthas, generally contain higher levels of impurities than reformate and will consequently require feed pretreatment to remove contaminants which adversely affect catalyst action, especially N, S and diene species. Removal of these species can be effected when necessary by conventional treatments such as fractionation, adsorption and/or hydrotreating/stripping.

Reformate streams will typically come from a fixed bed, swing bed or moving bed reformer. Although capital and process operating economics are favored by not using a reformate splitter with the reformer effluent going straight to the alkylation reactor after passing through the separators, a preferred embodiment of the invention uses a splitter to produce a cut containing at least 5 wt. percent benzene although cuts with at least 15 wt. percent or more, e.g. 25, 30, 35 or 40 wt. pct. benzene with the balance of aromatics being toluene and xylenes, are very useful feeds depending on the availability of propylene in the refinery. With limited propylene availability, an aromatic reformer stream with 5 to 20 wt. pct. Benzene, e.g. 7-15 wt. pct., is useful in a configuration with a reformate splitter and a propylene stabilizer. In addition to the aromatics, the reformate will typically contain paraffins and naphthenes with carbon numbers appropriate to the cut points selected for the reformate feed and on the reformer product fractionator, if used. Generally, the carbon numbers of the paraffins and naphthenes in the feed to the present process will be in the range of C5 to C8 although high cut points for the reformer feed or product may allow higher carbon numbers to be present.

The most useful reformate fraction is a heart-cut reformate. This is preferably a reformate having a narrow boiling range, i.e. a $C_6$ or $C_6/C_7$ fraction. This fraction is a complex mixture of hydrocarbons recovered as the overhead of a dehexanizer column downstream from a depentanizer column. The composition will vary over a range depending upon a number of factors including the severity of operation in the reformer and the composition of the reformer feed. These streams will usually have the $C_5$, $C_4$ and lower hydrocarbons removed in the depentanizer and debutanizer. The heart-cut reformate will therefore usually contain at least 50 wt. % $C_6$ hydrocarbons, and preferably at least 60 wt. % $C_6$ hydrocarbons.

By boiling range, these benzene-rich fractions can normally be characterized by an end boiling point of about 120° C. (250° F.)., and preferably no higher than about 110° C. (230° F.). Preferably, the boiling range falls between 40° and 100° C. (100° F. and 212° F.)., and more preferably between the range of 65° to 95° C. (150° F. to 200° F.) and even more preferably within the range of 70° to 95° C. (160° F. to 200° F.).

The compositions of two typical heart cut reformate streams are given in Tables 1 and 2 below. The reformate shown in Table 2 is a relatively more paraffinic cut but one which nevertheless contains more benzene than the cut of Table 1, making it a very suitable substrate for the present alkylation process.

TABLE 1

| C6-C7 Heart Cut Reformate | |
|---|---|
| RON | 82.6 |
| MON | 77.3 |
| Composition, wt. pct. | |
| i-$C_5$ | 0.9 |
| n-$C_5$ | 1.3 |
| $C_5$ napthenes | 1.5 |
| i-$C_6$ | 22.6 |
| n-$C_6$ | 11.2 |
| $C_6$ naphthenes | 1.1 |
| Benzene | 32.0 |
| i-$C_7$ | 8.4 |
| n-$C_7$ | 2.1 |
| $C_7$ naphthenes | 0.4 |
| Toluene | 17.7 |
| i-$C_8$ | 0.4 |
| n-$C_8$ | 0.0 |
| $C_8$ aromatics | 0.4 |

TABLE 2

| Paraffinic C6-C7 Heart Cut Reformate | |
|---|---|
| RON | 78.5 |
| MON | 74.0 |
| Composition, wt. pct. | |
| i-$C_5$ | 1.0 |
| n-$C_5$ | 1.6 |
| $C_5$ napthenes | 1.8 |
| i-$C_6$ | 28.6 |
| n-$C_6$ | 14.4 |
| $C_6$ naphthenes | 1.4 |
| Benzene | 39.3 |
| i-$C_7$ | 8.5 |
| n-$C_7$ | 0.9 |
| $C_7$ naphthenes | 0.3 |
| Toluene | 2.3 |

Olefin Stream

The light olefins used as the feed for the present process are normally obtained by the catalytic cracking of petroleum feedstocks to produce gasoline as the major product. The catalytic cracking process, usually in the form of fluid catalytic cracking (FCC) is well established and, as is well known, produces large quantities of light olefins as well as olefinic gasolines and by-products such as cycle oil which are themselves subject to further refining operations. The olefins which are primarily useful in the present process are the lighter olefins from ethylene up to butene (C2 to C4 olefins); although the heavier olefins may also be included in the processing, they can generally be incorporated directly into the gasoline product where they provide a valuable contribution to octane. For this reason as well as their ready availability in large quantities in a refinery, mixed olefin streams such a FCC Off-Gas streams (typically containing ethylene, propylene and butenes) may be used although mixed light olefin streams may be obtained from other process units including cokers, visbreakers and thermal crackers with intervening fractionation to remove the heavier components.

The present process is highly advantageous in that it will operate readily not only with butene and propylene but also with ethylene and thus provides a valuable route for the conversion of this cracking by-product to the desired gasoline product. Olefinic streams containing principally propylene as the olefinic component are preferred although minor quantities of ethylene and butene are not disadvantageous. Petrochemical grade propylene streams are particularly preferred. Conversion of the $C_3$ olefin fraction from the cracking process provides a direct route to isopropyl-substituted alkylaromatics which are so highly desirable in gasoline from the view point of boiling point and octane.

The presence of diolefins which may be found in certain refinery streams such as those from thermal cracking is not desirable in view of their tendency to form high molecular weight polymerization products which indicates that their removal in a diolefin saturation unit is recommended.

The compositions of two typical FCC gas streams is given below in Tables 3 and 4, Table 3 showing a light FCC gas stream and Table 4 a stream from which the ethylene has been removed in the gas plant for use in the refinery fuel system. Table 5 gives the composition of a typical petrochemical grade stream of the preferred type.

TABLE 3

FCC Light Gas Stream

| Component | Wt. Pct. | Mol. Pct. |
|---|---|---|
| Ethane | 3.3 | 5.1 |
| Ethylene | 0.7 | 1.2 |
| Propane | 14.5 | 15.3 |
| Propylene | 42.5 | 46.8 |
| Iso-butane | 12.9 | 10.3 |
| n-Butane | 3.3 | 2.6 |
| Butenes | 22.1 | 18.32 |
| Pentanes | 0.7 | 0.4 |

TABLE 4

$C_3$-$C_4$ FCC Gas Stream

| Component | Wt. Pct. |
|---|---|
| 1-Propene | 18.7 |
| Propane | 18.1 |
| Isobutane | 19.7 |
| 2-Me-1-propene | 2.1 |
| 1-Butene | 8.1 |
| n-Butane | 15.1 |
| Trans-2-butene | 8.7 |
| Cis-2-butene | 6.5 |
| Isopentane | 1.5 |
| C3 Olefins | 18.7 |
| C4 Olefins | 25.6 |
| Total Olefins | 44.3 |

TABLE 5

Petrochemical Grade Propylene Stream

| Component | Wt. Pct. |
|---|---|
| Propylene | 99.6+ |
| Propane | 0.4 |

It may be desirable to include a propylene stabilizer such as a flash drum or other suitable equipment in the system in order to control the RVP of the Reformate Alkylation Product by removing any C2 which may be present in the olefin feed.

As noted here, the light olefinic stream typically contains light paraffins in the same boiling range from the distillation step if any. The paraffins act as a diluent for the reaction, serving to carry off heat of reaction and so helping to prevent any undesirable exotherm in the catalyst bed.

Product Formation

During the process, a number of mechanistically different reactions take place. The principle reactions taking place will be alkylation and transalkylation reactions between the aromatics and the olefins. These reactions will predominate significantly over olefin oligomerization since the aromatics are readily sorbed onto the catalyst and preferentially occupy the catalytic sites making olefin self-condensation reactions less likely to occur as long as sufficient aromatics are present. Reaction rates and thermodynamic considerations also favor direct olefin-aromatic reactions. Whatever the involved mechanisms are, however, a range of alkylaromatic products can be expected with varying carbon numbers.

The objective normally will be to produce fuel products having a carbon number no higher than 14 and preferably not above 12 since the most valuable gasoline fuel hydrocarbons are at $C_7$-$C_{10}$ from the viewpoint of volatility including RVP and engine operation at varying conditions. Di- and tri-alkylation is therefore preferred since with the usual $C_2$, $C_3$ and $C_4$ olefins and a predominance of benzene in the aromatic feed, alkylaromatic products with carbon numbers from about 10 to 14 are readily achievable. Depending on the feed composition, operating conditions and type of unit, the product slate may be varied with optimum conditions for any given product distribution being determined empirically. Control of product T90 and end point, however, may point towards a need to control conditions more closely to exclude the C10+ products which tend to increase the T90 if present in excessive amounts so that with propylene streams, it is better to limit the degree of alkylation to mono- and di-alkylation so as to maintain the carbon number at no more than 12 and preferably no more than 9. The dialkylated, tri-alkylated and polyalkylated benzenes however, have high blending octane numbers and provided gasoline T90 specifications can be observed, the inclusion of a limited amount of these more highly alkylated components can make a positive contribution to product octane.

With the staged olefin introduction, the initial reaction between the benzene and the olefin will be mono-alkylation and with the introduction of successive amounts of olefin between successive catalyst beds, additional alkyl groups will tend to be introduced onto the aromatic nuclei at which point, transalkylation will initiate itself to achieve an equilibrium within each successive bed. Transalkylation is in fact desirable because it tends to reduce the level of polyalkylation and, in so doing, reduces the proportion of higher boiling components in the product which, in turn leads to a lower product endpoint, desirable for motor gasolines. The relative incidence of transalkylation can be promoted by operating at a relatively higher temperature and with interstage injection of olefin. The choice of catalyst may also be significant as discussed below.

Catalyst

The catalysts used in the present process contain, as their essential catalytic component, a molecular sieve of the MWW type. These catalysts and their adaptability to use in reformate alkylation is described fully in U.S. 2006/0194998, to which reference is made for a description of the catalysts, their method of synthesis and formulation.

The MWW family of zeolites is currently known to include a number of zeolitic materials such as PSH 3 (described in U.S. Pat. No. 4,439,405), MCM-22 (described in U.S. Pat. No. 4,954,325), MCM-36 (described in U.S. Pat. No. 5,250,277), MCM 49 (described in U.S. Pat. No. 5,236,575), MCM 56 (described in U.S. Pat. No. 5,362,697), SSZ 25 (described in U.S. Pat. No. 4,826,667), ERB-1 (described in U.S. Patent No. EP 029302), ITQ-1 (described in U.S. Pat. No. 6,077,498), ITQ-2 (described in WO 97/17290), UZM-8 (described in U.S. Pat. No. 6,756,030). Of these, the four significant members of for use as aromatics alkylation and transalkylation catalysts are MCM-22, MCM-36, MCM-49, and MCM-56 with preference given to MCM-22 and MCM-49. It has been found that the MCM-22 or MCM-49 catalysts may be either used fresh, that is, not having been previously used as a catalyst or alternatively, regenerated catalyst may be used. Regenerated catalyst may be used after it has been used in any of the catalytic processes for which it is suitable, including the present process in which the catalyst has shown itself to remain active even after multiple regenerations. It may also be possible to use MWW catalysts which have previously been used in other commercial processes and for which they are no longer acceptable, for example, catalyst which has previously been used for the production of aromatics such as ethylbenzene or cumene, normally using reactions such as alkylation and transalkylation, as described in U.S. 2006/0194998.

Although larger pore size catalysts such as zeolites Y, USY, ZSM-12, and beta, can be used as the transalkylation catalyst, especially when they exhibit higher activity (higher alpha value), the selectivity of the MWW zeolites towards the less alkylated aromatics makes them particularly useful in the production of low end point gasoline. While the addition of a product fractionator to remove the heavy ends would enable gasoline specifications to be met, it is obviously desirable to avoid the increased capital and operating costs that would result from such an addition and for this reason, the use of the MWW zeolites functioning in both the alkylation and transalkylation roles is preferred. In addition, catalyst loading diagrams are simplified when using only the MWW zeolites in the process.

At low aromatic:olefin ratios, typically below 1.5, zeolites other than the preferred MWW zeolites tend to deactivate more quickly and they also have lower selectivity to the less alkylated products, with the result that high product endpoints may be encountered.

The catalysts for use in the present process will conventionally contain a matrix material or binder in order to give adequate strength to the catalyst as well as to provide the desired porosity characteristics in the catalyst. Catalyst formulation from the zeolite crystal will typically be as described in U.S. 2006/0194998. Zeolite:binder ratios will typically vary from 20/80 to 80/20 zeolite/binder with preference given to the higher zeolite catalysts above 50/50 in the finished catalyst. The catalyst will typically be formed into shapes such as spheres, cylinders, hollow cylinders, pellets, trilobes or quadrulobes; conventional equipment and techniques may be used for this purpose.

Catalyst regeneration may conveniently be carried out by air oxidation techniques similar to those used with other zeolite catalysts. MCM-22 and other catalysts of this family may be regenerated after catalytic use for example, in the present process and may also be reconditioned as described in U.S. 2006/0194998.

If a guard bed is used, the catalyst in it will normally be the same catalyst used in the alkylation reactor as a matter of operating convenience but this is not required: if desired another catalyst or sorbent to remove contaminants from the feed may used, typically a cheaper guard bed sorbent, e.g. a used catalyst from another process or alumina. The objective of the guard bed is to remove the contaminants from the feed before the feed comes to the reaction catalyst and provided that this is achieved, there is wide variety of choice as to guard bed catalysts and conditions useful to this end. The volume of the guard bed will normally not exceed about 20% of the total catalyst bed volume of the unit.

While the zeolite catalysts used in the present process are robust they do have sensitivity to certain contaminants (the conventional zeolite deactivators), especially organic compounds with basic nitrogen as well as sulfur-containing organics. It is therefore preferred to remove these materials prior to entering the unit if extended catalyst life is to be expected. If required, for instance, with the light olefin stream, scrubbing with contaminant removal washes such as water, caustic, MEA or other amines or aqueous wash liquids will normally reduce the sulfur level to an acceptable level of about 10-20 ppmw and the nitrogen to trace levels at which it can be readily tolerated. The zeolite catalyst does not require the presence of water in order to maintain activity and therefore the feed may be dried before entering the unit. The present zeolite catalysts, however, may readily tolerate up to about 1,000 ppmw water although levels above about 800 ppmw may reduce activity, depending on temperature so that a drier may be desirable as pre-treat.

Process Parameters

The present process is operated under a regime which maintains the aromatic component—initially the benzene-containing stream and subsequently, the alkylated benzene stream, in the liquid phase: supercritical conditions with respect to this reactant are to be avoided in order to minimize olefin consumption (vapor phase conditions may tend to favor undesirable side reactions such as the formation of higher molecular weight species, polyalkylaromatics, biphenyls, etc. Temperature and pressure are therefore selected to this end.

In general terms, the temperature (reactor inlet) will be from about 120° to 350° C. (about 250 to 660° F.) and in most cases between 150° and 250° C. (about 300 to 480° F.). Temperatures of 160° to 220° C. (about 375° to 425° F.) will normally be found optimum for propylene feeds with a range of 175 to 200° C. (about 350 to 390° F.), e.g. approximately 200° C. (about 390° F.) being seen as optimal under an appropriate pressure to maintain liquid phase operation with a temperature increase across each bed of 25° C. being regarded as an optimal value. The use of low temperatures of this magnitude is favored to preclude excessive cracking of the feeds, particularly of paraffins present in the reformate which, as noted below, may undergo isomerization to higher octane products. Pressures will normally be dependent on unit constraints but usually will not exceed about 10,000 kPag (about 1450 psig) with low to moderate pressures, normally not above 7,000 kPag (about 1,000 psig) being favored from equipment and operating considerations although higher pressures are not unfavorable in order to maintain liquid phase operation. Pressures in the range of 3,500 to 4,000 kPag (about 500 to 570 psig) are quite adequate and are suitable for use in many moderate pressure process units. Space velocities can be quite high, giving good catalyst utilization. Space velocities are normally in the range of 0.25 to 5 $hr^{-1}$ LHSV for the reformate feed, in most cases, 1 to 2 $hr^{-1}$ LHSV. Optimum conditions may be determined empirically, depending on feed composition, catalyst aging and unit constraints.

Benzene conversion is to be maximized in order to reduce the benzene content in the final product with certainty below the required levels to meet regulatory specifications. Conversion of at least 90% and higher is the norm, with conversions as high as 92% or higher, e.g. 95% being achievable. Lower conversions (70-90%) are easily obtainable but may not produce sufficient benzene reduction to produce on-spec mogas. High benzene conversion is favored by the use of higher propylene:benzene ratios but is relatively independent of temperature and space velocity with pressure being set to maintain liquid phase conditions. High olefin conversion is characteristic of the reaction with olefin conversion of at least 95% (process is single pass) being the norm in practice with 99% or higher being most desirable.

The reaction is carried out in once-through (single pass) mode for the aromatic stream. The presence of the heavy polyalkylated products in recycle inhibits benzene conversion and so recycle is inappropriate for achieving benzene levels of less than 1 percent in the product. It is hypothesized that the polyalkylated species may become preferentially sorbed on the catalyst and so preclude access to the active sites on the zeolite by the benzene. Recycle of unreacted benzene from the product splitter following a reaction at relatively low conversion has also been found to be an unattractive option since the presence of benzene co-boilers in the recycle stream unduly increases the size of the equipment. Thus, high conversion in single pass operation is the preferred option.

The alkylation reaction is markedly exothermic with heat release of about 2300 kJ/kg (~1000 BTU/lb) propylene; in order to avoid an undesirable exotherm, cooling is provided, either in the form of cooled olefin injected between beds or stages, by interstage cooling, e.g. by water-cooled heat exchanger, air-cooled heat exchanger, feed heat exchanger, or by the use of suitable reactor design. For example, a water-cooled tubular reactor of the type commonly used for the Polygas reaction (light olefin polymerization over SPA catalyst) could be used to maintain a desired temperature profile in the reactor. If olefin quench is used, the temperature of the olefin stream should be at least 20° C. lower than that of the reactant stream at the point of injection. Multiple bed operation will normally be used in order to deal with the heat release and typically, from one to six beds will be used although at least two, e.g., three or four or even more, will normally be adequate provided that adequate measures are taken to control excessive bed exotherm. Multiple bed operation has also been found to have a favorable effect on benzene conversion with multiple injection points leading to higher benzene conversion at a fixed propylene to aromatic ratio; while benzene conversion can be brought to levels of about 80 pct. at a propylene:aromatic ratio of 1.3:1 using a single olefin injection point, the same conversion can be achieved at a ratio of less than 1.0 when using multiple, e.g. three, injection points, If sulfur is present in the olefin feed, e.g. in FCC off-gas, in the form of various sulfur-containing compounds e.g. mercaptans, its effect as a catalyst poison is unlikely to be significant since at the preferred higher temperatures of about 180° C. or higher, e.g. 200° C., 220° C., the sulfur compounds are desorbed from the zeolite.

The ratio between the olefin and aromatic feed components is normally chosen to achieve the desired process objective of benzene reduction at high conversion while maintaining olefin consumption at a low level consistent with achieving benzene conversion, olefin conversion and other objectives. In the reformate alkylation chemistry, propylene is the limiting reactant and always reacts to completion. Therefore, when the ratio of propylene to aromatic is increased, benzene conversion increases and there is no opportunity for recycle of unreacted propylene. Generally, it is preferred that the ratio of olefins to benzene should be greater than 1:1 molar although operating below 1:1 will not damage the catalyst. In most cases, the molar ratio should be at least 1.25:1 olefin:benzene and for the highest benzene conversion levels, ratios of at least 2:1, even as high as 3:1 may be needed although conversion levels of over 90 pct, e.g. 95% or higher can be achieved with ratios of approximately 1.3 to 1.5, especially when resort is made to multiple olefin injection points.

Figure 8A:
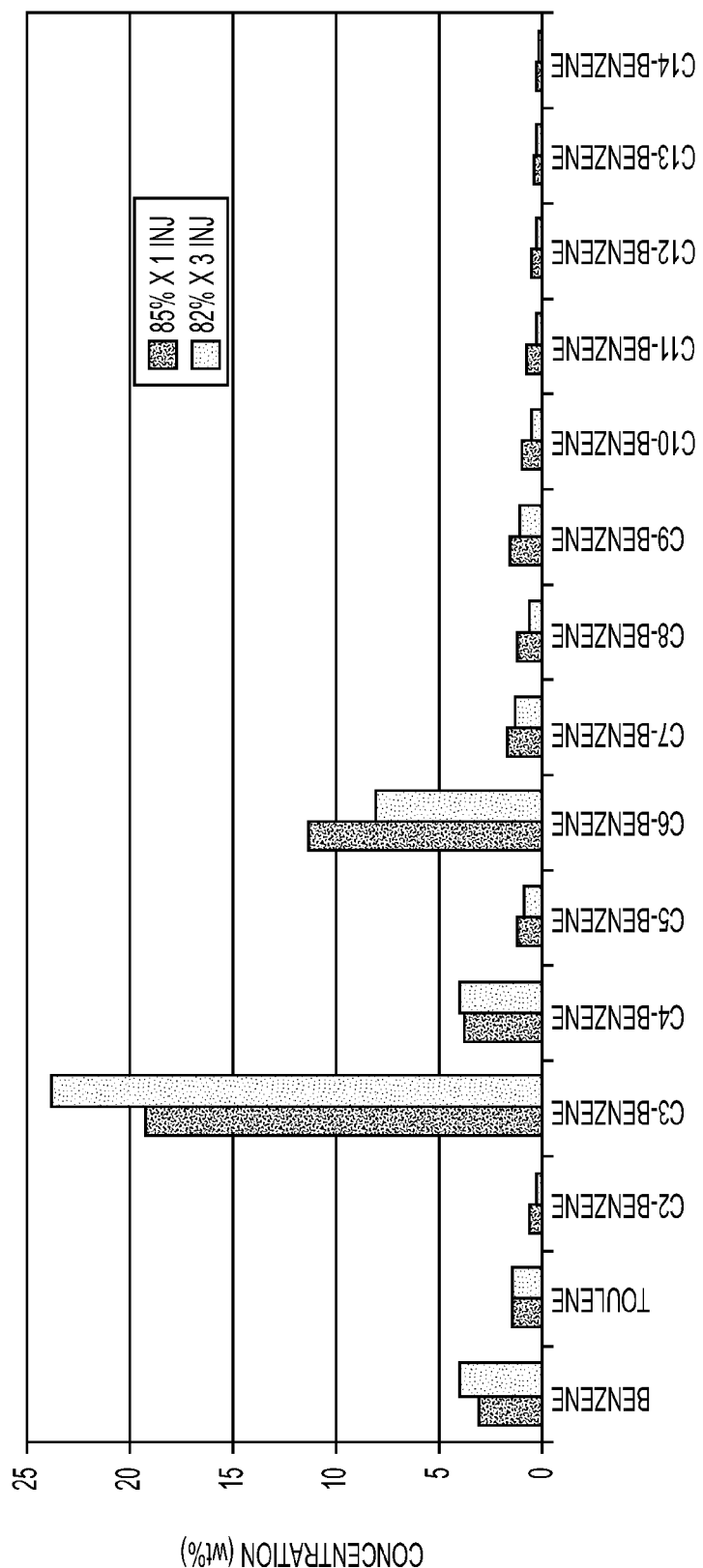
FIGS. 8A and 8B are graphs showing the relative amounts of heavy ends in the alkylation product from processes using one and three olefin injection points.
Figure 8B:
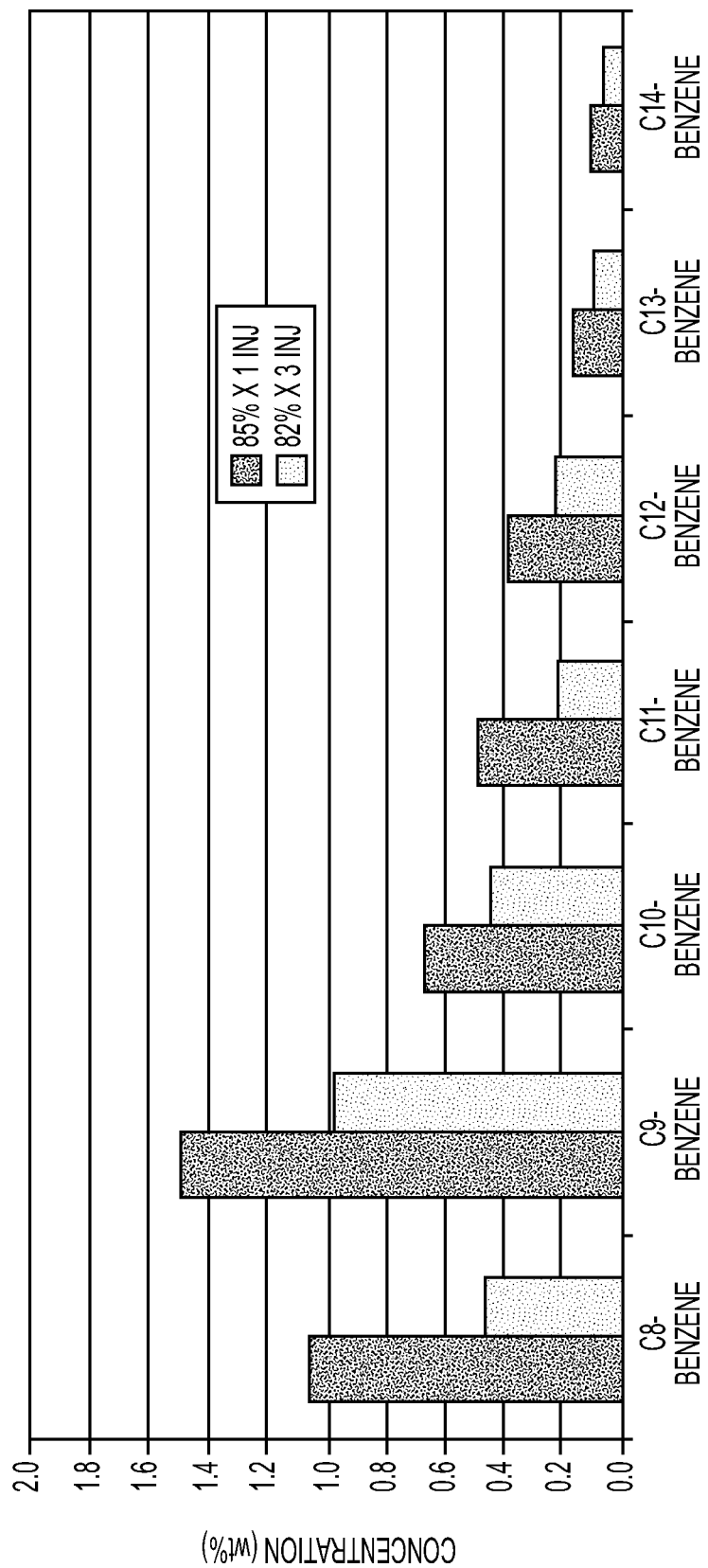

Multiple olefin injection points along the reaction path, preferably three or more, are desirable from the viewpoint of reducing the volume of heavy polyalkylates boiling above the gasoline boiling range, typically, C8-benzenes and higher. FIGS. 8A and 8B show the effect of the number of injection points on product distribution. FIG. 8A compares the 2D-GC/MS analysis of two pilot unit runs and FIG. 8B highlights the heavy molecules that are difficult to distinguish in FIG. 8A. The data were obtained using the same sulfolane raffinate feed that contained 24.9 wt. pct. benzene and 5 wt. pct. toluene in each case. Benzene conversion in each case was similar (85%, 82%). The product made with the single olefin injection contained less C3-benzene and more of each detectable molecule heavier than C5-benzene than the multiple olefin injection product; the reduction of C6-benzene is very significant considering its proportion in the entire product.

Figure 9:
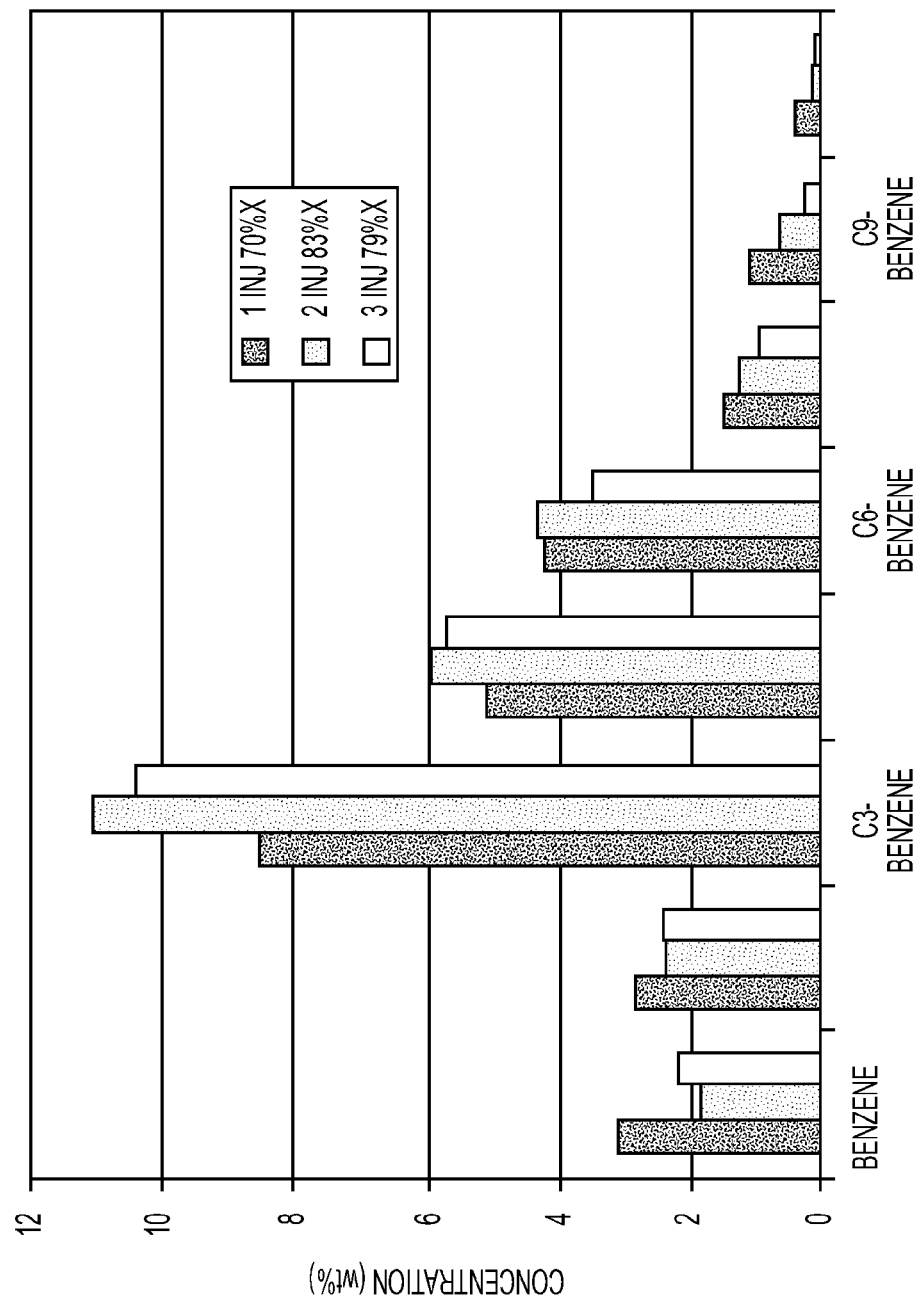
FIG. 9 is a graph showing the relative amounts of heavy ends in the alkylation product from processes using one, two and three olefin injection points.

FIG. 9 giving the summary results from a similar pilot plant study using one, two and three olefin injection points with identical feeds (synthetic reformate from chemical grade hexane blended with 11.2 wt % benzene and 7.4 wt % toluene), shows that a similar trend occurred. The figure gives three sets of 2D-GC/MS data from the study at similar benzene conversions. The results in the figure show that for C6-benzene molecules and heavier, the three olefin injection experiment produced less heavy molecules than the single olefin and two olefin injection experiments even though the single olefin injection experiment was operated at the lowest benzene conversion which in itself would be expected to result in the least amount of heavy molecular weight species. However, as indicated in the figure, the lowest benzene conversion actually had the greatest number of high boiling components, further illustrating that heavies production can be reduced with multiple olefin injection points. Analysis of results from the comparative studies using single and multiple olefin injection points showed that the molecules present in the products were identical, although they existed in different concentrations with significantly less high molecular weight molecules when multiple injection points are used; no poly-aromatics were detected in the study using the synthetic reformate. Operation with multiple olefin injection points favors lighter products: with multiple olefin injection points, the formation of isopropyl benzene increases, and the formation of heavy di and tri-isopropyl benzene decreases. Also, less propylene is required to achieve the desired benzene conversion in the low conversion regime (around 80%) when multiple olefin injection points are used so that there is a significant benefit to operating with multiple injections at low (~80%) benzene conversion although this benefit is less perceptible at high benzene conversion (~95%) when the single reactor and multiple reactor curves converge. The formation of high boiling alkylation products can, however, be suppressed by the use of multiple olefin injection points even at high benzene conversions and so the multiple injection option remains the preferred mode of operation regardless of conversion.

The multiple injection points referred to here are arranged along the reaction path, that is, at intervals between the inlet to the first catalyst bed or reactor and the point where the reaction effluent leaves the last catalyst bed or reactor for the olefin. They are conveniently located between catalyst beds or between successive reactors, depending on the process equipment used.

By appropriate adjustment of the reaction conditions, the product distribution may be modified: shorter feed/catalyst contact times tend to a product distribution with lower molecular weight oligomers while relatively longer contact times lead to higher molecular weight (higher boiling products). So, by increasing feed/catalyst contact time, it is possible to produce products in the middle distillate boiling range, for example, an aromatic road diesel as well as kerojet blend stocks. Overall feed/catalyst contact time may be secured by operating at low space velocity or by providing recycle to the reactor.

Alkylation Product

The alkylation product will comprise alkylbenzenes, mainly mono-alkylbenzenes and dialkylbenzenes with lower amounts of the tri-alkylbenzenes and tetra-alkylbenzenes, in which the alkyl groups are determined by the alkylating species present in the light olefin stream. With the preferred propylene streams, the alkylation products in the reactor effluent along with light paraffins and cycloparaffins, will then comprise cumene (isopropylbenzene), di-isopropylbenzene, tri-isopropylbenzene and some tetra-isopropylbenzene The propylene will preferentially carry out the electrophilic substitution on benzene and toluene with lower conversion of xylenes due in part to steric effects. In compositional terms, the benzene/propylene alkylation products will be as follows as percentages of all propylbenzenes in the reactor effluent:

TABLE 6

Alkylation Products

| | Broad Range | Preferred Range |
|---|---|---|
| isopropylbenzene | 25-75% | 40-60% |
| di-isopropylbenzene | 20-60% | 30-50% |
| tri-isopropylbenzene | 5-20% | 5-10% |

The proportion of these products in the reactor effluent will, of course, vary according to the composition of the reformate feed as well as on the reaction conditions used: as the proportion of diluents such as paraffins increases so the proportion of alkylbenzene reaction products will decrease. The polyalkylated products are desirable for their favorable influence on product octane as shown in the following Table 7 which gives the estimated pure component octane data for the mono-, di- and tri-alkylated benzenes (alkyl=isopropyl).

TABLE 7

Alkylation Product Octane

| Component | Blending RON | Blending MON |
|---|---|---|
| Benzene | 99 | 91 |
| Iso-Pr-BZ | 132 | 124 |
| Di-Iso-Pr-BZ | 132* | 124* |
| Tri-Iso-Pr-BZ estimated | 132* | 124* |

During the course of the alkylation reaction, the proportion of polyalkylates increases progressively with increasing benzene conversion. The proportion of benzene in the reaction mixture decreases monotonically with conversion while the proportion of the initial mono-alkylated product increases up to a maximum at benzene conversion levels between about 65 and 85 wt. pct. after which it decreases quite sharply as the proportion of the di-alkylated product conversely increases from its onset at around 20 to 30 pct. conversion with a significant increase in the proportion of this product being observed at benzene conversions of at least 80 percent so that when the benzene conversion attains 90 percent or more, the amount of the di-isopropyl product is comparable to that of the mono-propyl; the tri-alkylated product remains at a low level until high conversion levels of around 80 wt. pct are attained at which point, the amount of this product in the mixture noticeably increases although only attaining low levels, typically around 0.02 wt. pct. at the most at benzene conversions over 90 percent. At benzene conversions of 95 percent or higher, the proportion of the di-isopropyl product can be higher than that of the mono-isopropyl.

The motor gasoline boiling range product of the process as well as of the final blended gasoline containing it as a blend component is characterized by the presence of these polyalkylated species which are not native either to straight run napthas or to FCC gasoline and, of course, are not native to other gasoline blend components such as alkylate (from iso-paraffins and olefins), hydrocrackate and polymer gasoline. For this reason, the high octane gasolines made from these alkylation products as blend components are seen as new types of motor gasoline, In the direct alkylation products, the amounts of the polyalkylated species will be as shown in Table 6 above, i.e., isopropylbenzene at 25-75%, typically 40-60%, di-isopropylbenzene at 20-60%, typically 30-50% and tri-isopropylbenzene at 5-20%, typically 5-10% (percentages by weight). The finished motor gasolines will have corresponding amounts depending on the amount of this component used in the blend, with higher proportions used in the higher octane grades (usually 80 or 83 pump octane in the U.S.) for achieving on-specification octane. As a typical measure, the proportion of reformate and the present alkylated reformate will compose about 10-25 wt. pct. of regular (87 pump octane) and 15-35 wt. pct. premium (93 pump octane) with intermediate figures for mid-grade (90 pump octane).

A notable aspect of the present process is that the octane rating of the alkylation product is greater than was expected from a consideration of the aromatic species present: an increase of some 12 percent may be achieved and increases of at least 5, 8, or 10 percent are demonstrated. It is hypothesized that straight or slightly branched chain paraffins present in the reformate are isomerized in the presence of the catalyst to produce iso-paraffins of higher octane number and that these, even if present in only minor amounts may make a positive contribution to product octane. Typically, the ratio of normal to iso-paraffins in the feed and product, respectively, decreases from about 0.5 to slightly less than 0.4 for $C_5$ paraffins, remains relatively constant for C6 paraffins and decreases from about 0.2 to a lower value of about 1.8 or so for C7s. Octane deltas typically range from 8 to 14 (RON) and from 7 to 12 (MON) with normal refinery feeds. Pump octane ((R+M)/2) improvements of 2 to 5 numbers can be achieved for the alkylate product. (All octane numbers in this specification are "clean", i.e. R is R+0 and M is M+0.)

Another notable feature of the present invention is that the alkylation causes a volume expansion of the gasoline boiling range product, typically of the order of 5 percent but possibly varying from about 2 up to about 8 percent (by volume) of the aromatic feed. In a typical case, a unit of nominal input rate of 6,000 m³/day (37,735 KBD) for the aromatic feed could be expected to produce 6,345 m³/day (39,906 KBD) of alkylation product in the gasoline boiling range, representing a useful increase of gasoline product volume.

EXAMPLES

Examples 1-3

Three reformate samples were alkylated with a propylene stream. The reformate streams were a light cut with 27 wt. % benzene, a light cut with 52 wt. % benzene and a full range reformate with only 5 wt. % benzene. Their compositions are set out in Tables below. The propylene stream was a petrochemical grade stream of 99 wt. pct. propylene and 1 wt. pct. propane.

The alkylation was carried out in a pilot plant under the conditions described below using a catalyst of MCM-49 (80/20 zeolite/alumina) 1.27 mm (0.05 inch) quadrulobe. This same type of catalyst was also used in all the Examples below. A range of benzene conversions were achieved with the different reformate feeds.

Table 8 shows the operating conditions for pilot unit studies with the three different reformate feeds. All studies were operated in once-through mode with an inlet temperature of 205 C (400° F.) and 6550–7000 kPag (950-1000 psig) reactor pressure. These pilot units were set up with one propylene injection point located at the reactor inlet.

TABLE 8

Operating Conditions for Reformate Alkylation

| Operating Conditions | Light Reformate (27% Benzene) | Light Reformate (52% Benzene) | Full Reformate (5% Benzene) |
|---|---|---|---|
| Inlet temp., °C./°F. | 205/400 | 205/400 | 205/400 |
| Reactor Pressure, kPag/psig | 7000/1000 | 6550/950 | 6550/950 |
| Reformate LHSV, hr$^{-1}$ | 1.3 | 1.1-4.5 | 1.8 |

Figure 2:
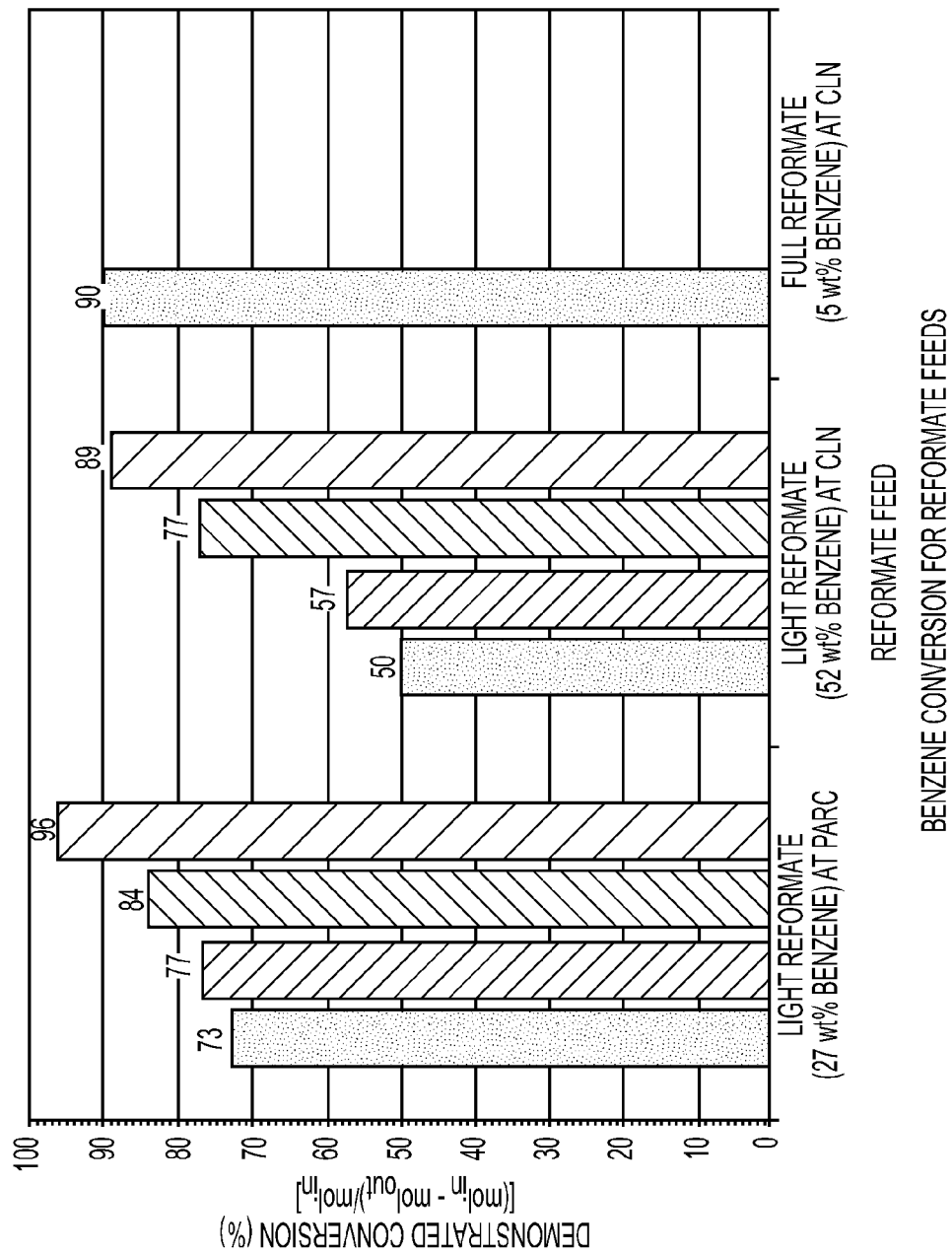
FIG. 2 is a graph showing the benzene conversion for different reformate feeds.

Benzene conversion was controlled by the amount of propylene fed in ratio to the aromatics in the reformate. Conversion is calculated based on a ratio of benzene moles reacted to benzene moles fed. FIG. 2 shows the steady state conversions achieved for the various feeds during these pilot studies. The study on light reformate with benzene concentrated to 27 wt % achieved a range of conversions from 73-96%. The study on light reformate with benzene concentrated to 52 wt % achieved a range of conversions from 50-89%. The study on full range reformate with a benzene concentration of 5 wt % was set at 90% conversion.

Table 9 lists the benzene conversions with the corresponding propylene to aromatics ratio (P:A, molar). To increase conversion to very high levels, the P:A ratio had to be increased more severely.

TABLE 9

Benzene Conversion vs P:A Ratio

| Light Reformate (27 wt % Benzene) | | Light Reformate (52 wt % Benzene) | | Full Reformate (5 wt % Benzene) | |
|---|---|---|---|---|---|
| BZ Conv. % | P:A | BZ Conv. % | P:A | BZ Conv. % | P:A |
| 73 | 0.93 | 50 | 0.49 | 90 | 2.78 |
| 77 | 1.01 | 57 | 0.61 | — | — |
| 84 | 1.45 | 77 | 1.02 | — | — |
| 96 | 2.9 | 89 | 1.42 | — | — |

Figure 3:
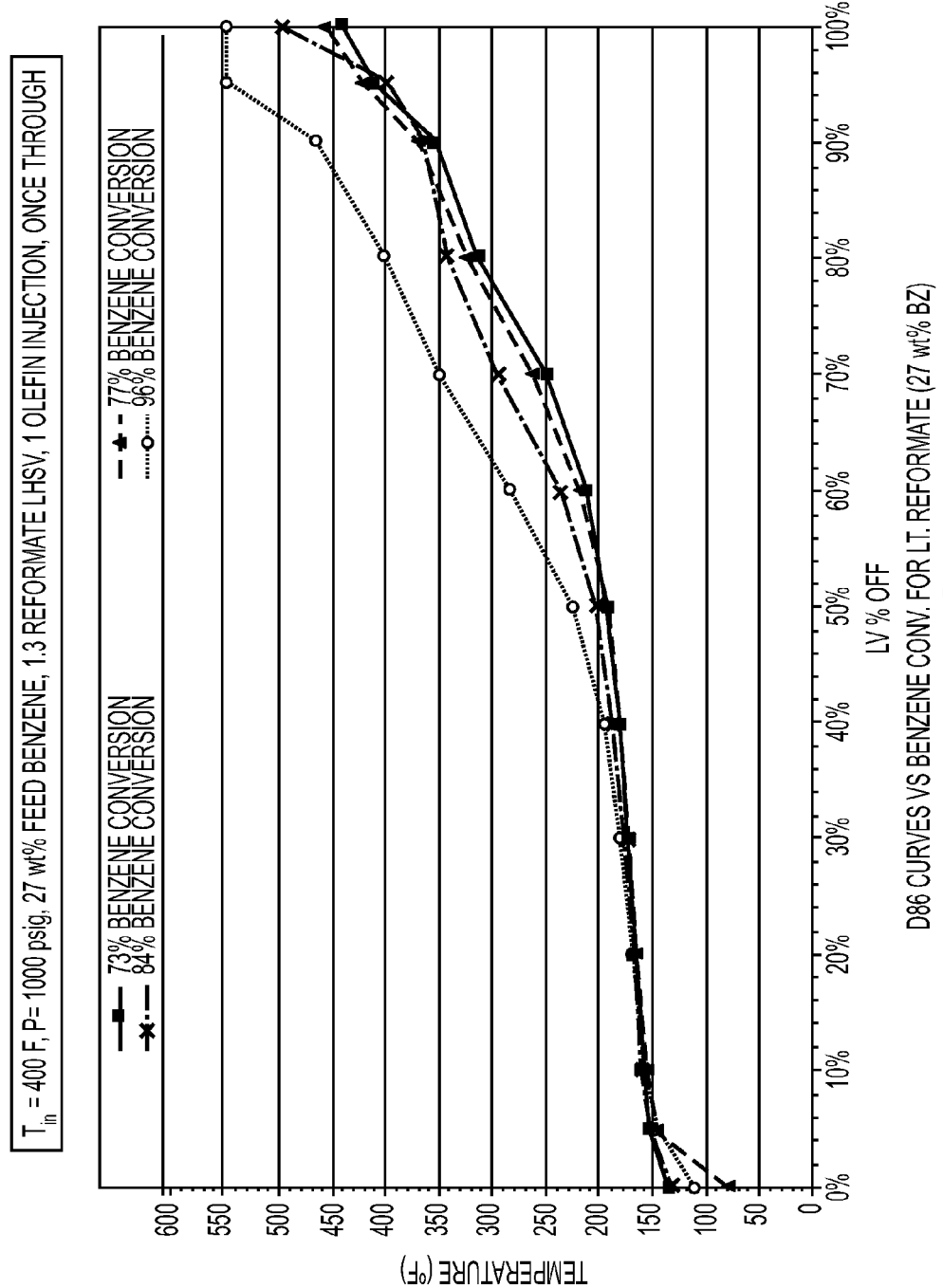
FIG. 3 is a graph showing the D86 Curves for different levels of benzene conversion for a light reformate feed (27 wt % benzene)
Figure 4:
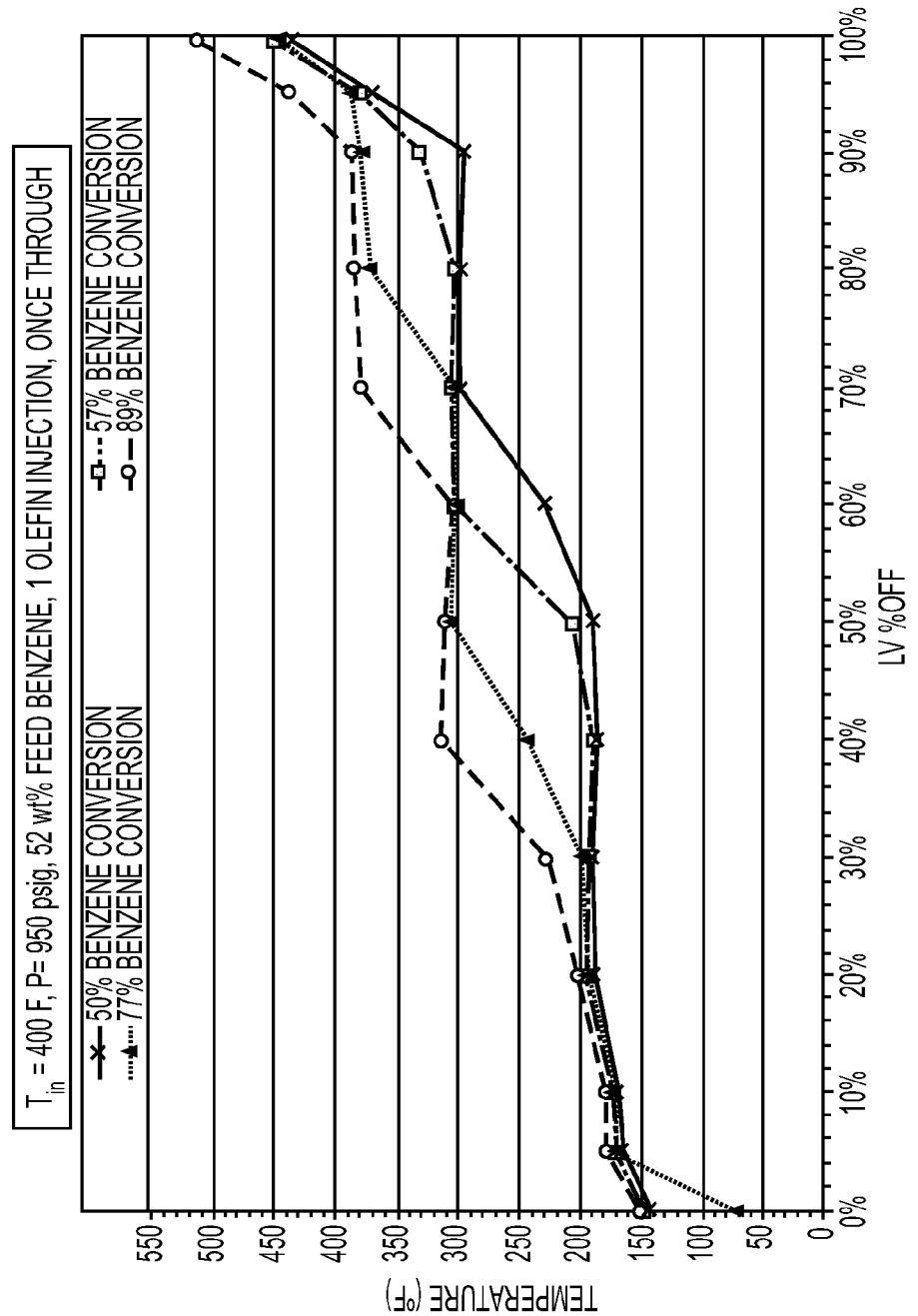
FIG. 4 is a graph showing the D86 Curves for different levels of benzene conversion for a light reformate feed (52 wt % benzene)

As propylene is fed at a higher ratio to aromatics, the aromatic molecules become heavier with the iso-propyl groups. The boiling points of the aromatic content rises. FIGS. 3 and 4 show the ASTM D 86 distillation curves as P:A and conversion increased for the two light reformate feeds.

Examples 4-5

The advantages of using interstage olefin injection were demonstrated using pilot plant units with one reactor with one olefin injection or three reactors with three olefin injection points, one before each reactor with the reformate flowing through the reactors in series.

The pilot unit operated with the liquid phase, single pass conditions shown in Table 10, using a constant aromatic:olefin ratio of 0.72:

TABLE 10

Unit Operating Conditions

| | |
|---|---|
| T inlet, °C.(°F.) | 204 (400) |
| Pressure, kPag (psig) | 4140 (600) |
| Reformate WHSV | 2.7 |
| Feed | |
| Benzene (wt %) | 24.9 |
| Toluene (wt %) | 4.9 |
| Balance | Sulfolane Raffinate |
| Aromatic:Olefin Ratio | 0.72 |

Figure 5:
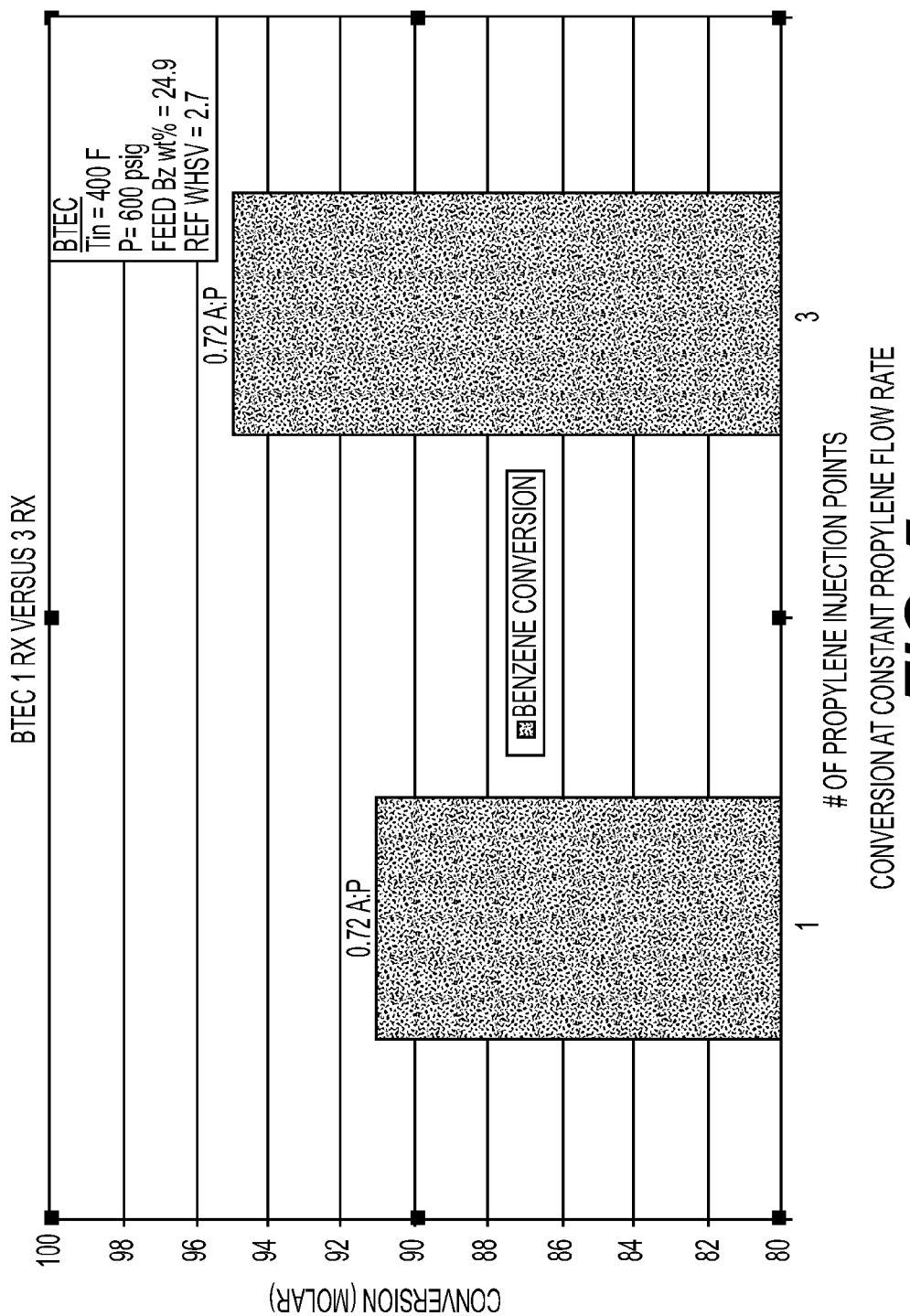
FIG. 5 is a graph showing the benzene conversion at constant propylene flow rate.

FIG. 5 shows the improvement in conversion with three olefin injection points compared to a single injection configuration. While the overall propylene feed rate is kept constant between the two configurations, the three olefin injection configuration shows an improvement in benzene conversion at the same aromatic to propylene molar ratio (A:P). The Simulated Distillations (ASTM D 2887) show that the reaction product from the three point injection configuration exhibits a lower temperature from 91-100% off with a favorable difference of approximately 17° C. (3° 0 F) at 100% off, indicating the potential to produce a gasoline product with a lower end point and T90 even with the higher conversion resulting from the 3-injection point configuration.

Figure 6:
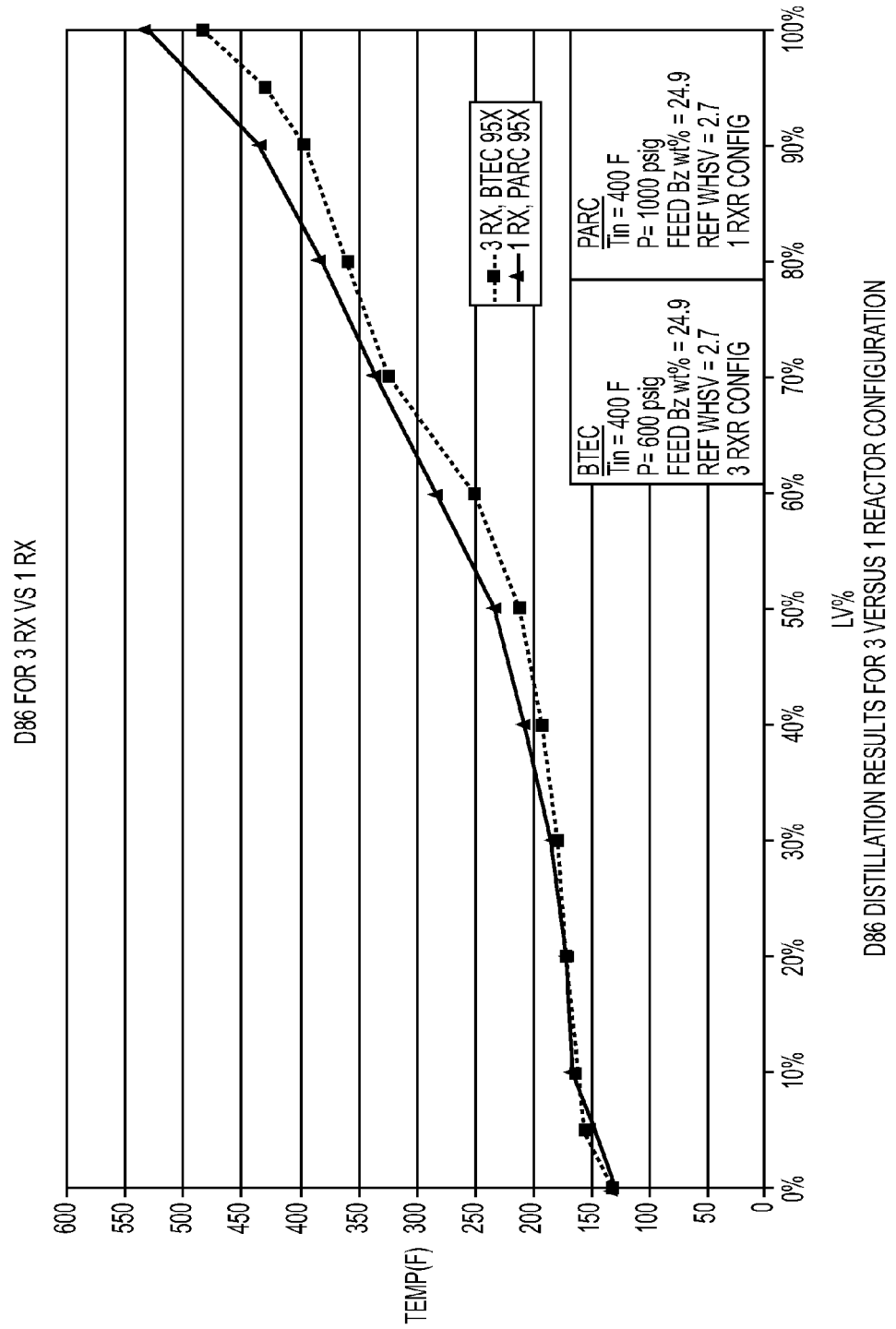
FIG. 6 is a graph showing the D86 Curves for different levels of benzene conversion for a light reformate feed (24.9 wt % benzene) in two different reactor configurations.

The data from the three reactor configuration were compared to a second single reactor pilot unit, running at similar unit conditions except for a pressure of 7000 kPag (1000 psig) and the same conversion. The results are seen in FIG. 6 with a confirmation of the advantages of a three reactor (three injection point) configuration (FIG. 6 data for the single reactor are a simulated distillation converted to D86 for ease of comparison).

Data from the second single reactor unit (7000 kPag) when compared with the results from the three-reactor unit (4140 kPag) showed that the final boiling point of the alkylated product was significantly lower for the three-reactor configuration (250° C./482° F. as against 278° C./533° F.). At the same time, this three-reactor unit had a propylene consumption of 0.6 WHSV compared to 1.0 WHSV for the single reactor configuration and there was a reduction of the volume of alkylation product boiling above 225° C. (437° F.): 10% 225° C.+ for the single reactor and 4% 225° C.+ for the three reactor, indicating that product end point can be effectively controlled by this multiple point olefin injection technique. The advantages are expected to be observed for any number of propylene injection points greater than one.

Examples 6-11

These Examples show that alkylation of the reformate provides an increased octane value for the product. Pilot unit studies have demonstrated a positive octane delta, the magnitude of which depends on benzene conversion and product cut point. The pilot unit, from which the data was presented from, is in a once through, single olefin injection configuration. The unit was running according to the following Table 11.

TABLE 10

Unit Operating Conditions

| | |
|---|---|
| Unit Conditions | |
| T inlet, C. (F.) | 204 (400) |
| Pressure, kPag (psig) | 7,000 (1,000) |
| Reformate WHSV | 2.7 |
| Feed | |
| Benzene (wt %) | 24.9 |
| Toluene | 4.9 |
| Balance | Sulfolane Raffinate |

The data in Table 12 below show octane data recorded in the pilot plant. All octane analyses were conducted by engine tests via D 2699 and ASTM D 2700. The results show that the magnitude of the increase in octane (both RON and MON) is dependent on the benzene conversion; the sensitivity, however, increases slightly with conversion.

TABLE 12

Reformate Octane Increase with Alkylation

| Ex. | P:A | RON | MON | ΔRON | ΔMON | (R + M)/2 | R − M |
|---|---|---|---|---|---|---|---|
| Feed | | 73 | 72.6 | | | 72.8 | 0.4 |
| BZ Conv. (% molar) | | | | | | | |
| 6 | 0.92 | 81.9 | 79.9 | 8.9 | 7.3 | 80.9 | 2 |
| 7 | 1.01 | 83.1 | 80.9 | 10.1 | 8.3 | 82 | 2.2 |
| 8 | 1.5 | 84.1 | 81.5 | 11.1 | 8.9 | 82.8 | 2.6 |
| 9 | 2.16 | 85.9 | 82.8 | 12.9 | 10.2 | 84.3 | 3.1 |
| 10 | 2.96 | 85.2 | 82.7 | 12.2 | 10.1 | 83.9 | 2.5 |
| 11 | 3.04 | 85.4 | 83 | 12.4 | 10.4 | 84.2 | 2.4 |
| 96% Conv 200° C. Cut | | 74.4 | 72.8 | 1.4 | 0.2 | 73.6 | 1.6 |
| 96% Conv. 225° C. Cut | | 81.7 | 79.2 | 8.7 | 6.6 | 80.4 | 2.5 |

Figure 7:
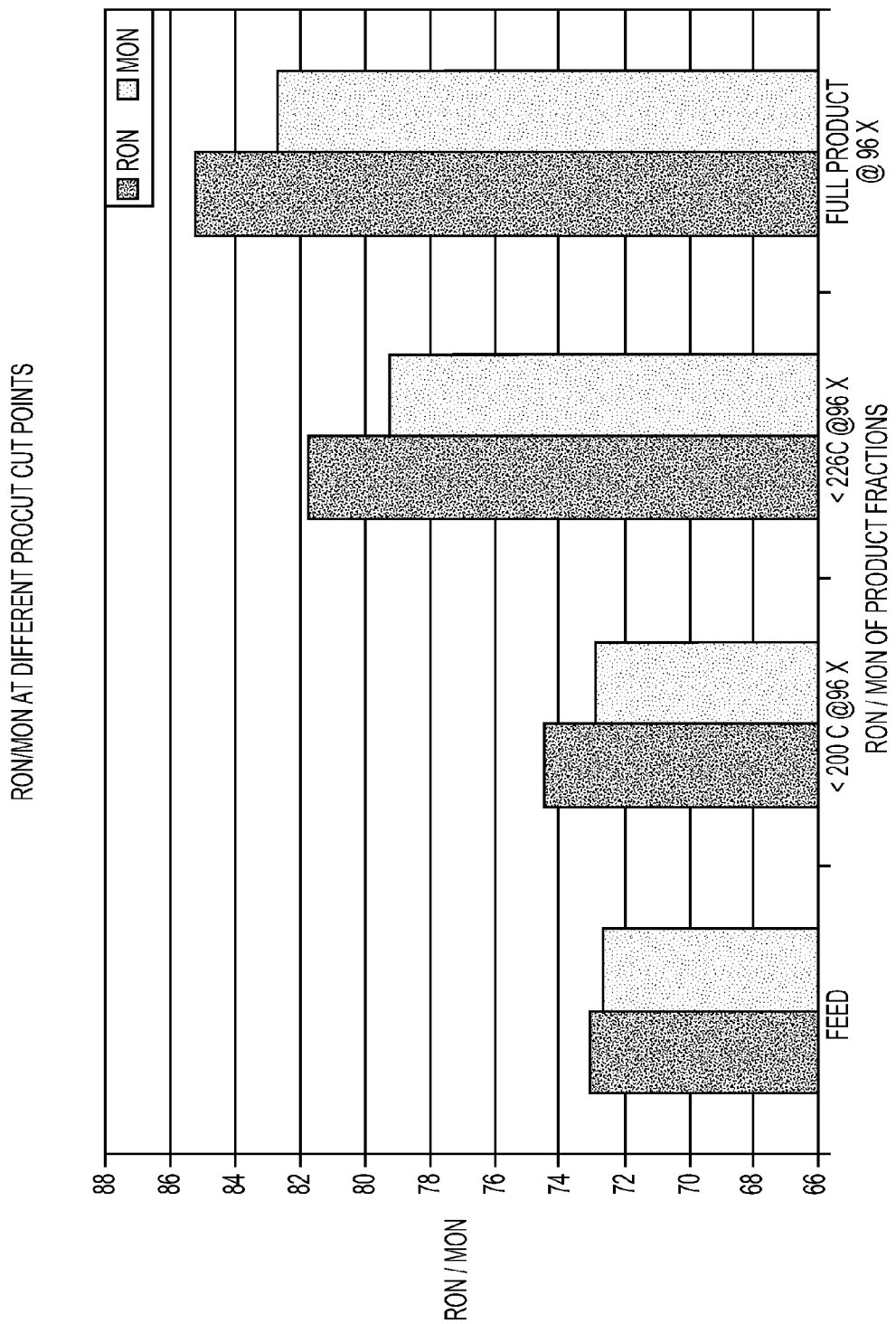
FIG. 7 is a graph showing RON/MON values for different product fractions.

FIG. 7 shows the measured RON and MON for the feed and for selected fractions of the 96% benzene conversion product. Engine tests were conducted on full reactor effluent and product that had been lab distilled to remove material above 200° C. and 225° C. The octane gain is a strong function of the cut point temperature with the full range reactor effluent demonstrating an average (RON+MON)/2 increase of approximately 11.5 above the unalkylated feed with smaller increases for the lower boiling cuts, indicating the potential for octane improvement with the increasing degree of alkylation as the alkylation occurs in series producing highly substituted aromatic rings that contribute largely to the octane increase. The sensitivity of the product increases with higher benzene conversions although this effect may be reduced by fractionation of the product with the possibility of offset by using the higher cut point which is still within the mogas endpoint specification (225° C.).

Examples 12-13

The staged pilot unit was run according to Table 13:

TABLE 13

| | Unit Operating Conditions |
|---|---|
| T inlet, C. (F.) | 204 (400) |
| Pressure, kPag (psig) | 4,137 (600) |
| Reformate WHSV | 2.7 |
| Feed | |
| Benzene (wt %) | 24.9 |
| Toluene | 4.9 |
| Balance | Sulfolane Raffinate |

The full range products were subjected to octane analysis again according to ASTM D 2699 and ASTM D 2700. Table 14 shows that staged olefin injection shows similar octane increases for a similar feed and unit conditions.

TABLE 14

Reformate Octane Increase with Staged Olefin Injection Alkylation

| Ex. | Benzene Conv. (% molar) | P:A | RON | MON | ΔRON | ΔMON |
|---|---|---|---|---|---|---|
| | Feed | | 73 | 72.6 | | |
| 12 | 82 | 0.87 | 82.2 | 79.7 | 9.2 | 6.7 |
| 13 | 95 | 1.41 | 85.5 | 82.9 | 12.5 | 9.9 |

Example 14

This Example shows that extremely low levels of residual benzene may be attained by use of multiple olefin injection points.

A light, benzene-spiked reformate containing 20.1 wt. pct. benzene and 5.9 wt % toluene was used as feed for the pilot unit during this study. It contained 20.1 wt % benzene. The balance was a mixture of primarily $C_5$-$C_7$ reformate paraffins. The propylene was refinery grade propylene of approximately 70/30 wt % propylene/propane.

The experimental runs used three propylene injection points except that Run 2-6-1 was simulated by reprocessing product collected during Run 2-3-3. All runs were made with an inlet temperature of 204 C (400 F) and 4140 kPag (600 psig). The catalyst load was 63 g/178.8 cc. The results are shown in Table 15 below.

TABLE 15

High Conversion Comparison

| | Run No. | | | |
|---|---|---|---|---|
| | 2-3-1 | 2-3-2 | 2-3-3 | 2-6-1 |
| C3= Injections | 3 | 3 | 3 | 6 |
| Reformate LHSV, hr$^{-1}$ | 1.5 | 2.1 | 2.1 | 2.1 |
| Reformate WHSV, hr$^{-1}$ | 3.4 | 4.9 | 4.9 | 5.0 |
| C3= LHSV, hr$^{-1}$ | 0.4 | 0.4 | 0.4 | 0.7 |
| C3 WHSV, hr$^{-1}$ | 0.6 | 0.4 | 0.5 | 0.9 |
| Fresh P:A, molar | 1.37 | 0.68 | 0.69 | 1.37 |
| Benzene in Product, wt. pct. | 0.29 | 3.88 | 4.62 | 0.05 |
| Benzene Conversion, molar | 0.98 | 0.78 | 0.74 | 1.00 |

The invention claimed is:

1. A process for producing a gasoline boiling range hydrocarbon product of low benzene content and controlled end point from a light, benzene-containing aromatic reformate feed stream comprising at least 15 weight percent benzene, which comprises alkylating the aromatic reformate feed stream in the presence of an MWW zeolite catalyst in at least two fixed catalyst beds in series in a single pass operation in the liquid phase with an alkylating agent consisting essentially of a propylene-containing olefinic feed stream comprising at least 50 weight percent propylene injected at the inlet to each catalyst bed under conditions of elevated temperature and pressure with a temperature (entry to first catalyst bed) from 120 to 250° C. and a pressure of at least 2500 kPag with the temperature of the propylene-containing olefinic feed at the injection point subsequent to the first catalyst bed below the temperature of the remaining reactant stream to provide quench for the reaction, at a molar ratio of the propylene-containing olefinic feed to the reformate feed of at least 1.0:1 to convert at least 90 weight percent of the benzene in the reformate feed to alkylbenzenes and produce an alkylated reaction product containing not more than 5 vol % of fractions boiling above 225° C.

2. A process according to claim 1 in which at least 95 weight percent of the benzene is converted to alkylbenzenes.

3. A process according to claim 1 in which the temperature (entry to first catalyst bed) is from 200 to 225° C.

4. A process according to claim 1 in which the pressure is sufficient to maintain liquid phase conditions and at least 4000 kPag.

5. A process according to claim 1 in which the amount of benzene in the product is not more than 1.3 volume percent.

6. A process according to claim 5 in which the amount of benzene in the product is not more than 1.0 volume percent.

7. A process according to claim 6 in which the amount of benzene in the product is not more than 0.6 volume percent.

8. A process according to claim 1 in which the benzene content of the reformate feed is at from 20 to 50 weight percent.

9. A process according to claim 1 in which the MWW zeolite catalyst is an MCM-22 catalyst.

10. A process according to claim 1 in which the molar ratio of the propylene-containing olefinic feed to the reformate feed is from 1.0:1 to 3:1.

11. A process according to claim 1 in which the temperature of the propylene-containing feed stream is at least 10° C. below the temperature of the remaining reactant stream at the point of injection of the propylene-containing feed stream.

12. A process according to claim 1 in which the alkylation reaction product comprises mono-, di- and tri-substituted isopropyl benzenes.

13. A process according to claim 1 in which the molar ratio of the propylene-containing olefinic feed to the reformate feed is at least 2.0:1.

14. A process according to claim 13 in which the molar ratio of the propylene-containing olefinic feed to the reformate feed is from 2:1 to 3:1.

15. A process for producing a gasoline boiling range hydrocarbon product having a benzene concentration of not more than 1 volume percent and controlled end point from a reformate feed having a benzene concentration of at least 20 weight percent which comprises alkylating the reformate feed in an alkylation reactor in the presence of an MWW zeolite catalyst in at least two fixed catalyst beds in a single pass operation in the liquid phase with an alkylating agent consisting essentially of a propylene-containing olefinic feed stream comprising at least 60 weight percent propylene injected at the inlet to each catalyst beds bed at a reactor inlet temperature from 200 to 250° C. and a pressure sufficient to maintain liquid phase conditions and from 4,000 to 10,000 kPag (reactor inlet), at a space velocity of 1 to 5 LHSV hr.−1 with a molar ratio of propylene-containing olefinic stream to reformate stream of at least 1.0:1 and with the temperature of the propylene-containing olefinic feed at the injection point subsequent to the first catalyst bed below the temperature of the remaining reactant stream to provide quench for the reaction, to convert at least 90 weight percent of the benzene in the reformate feed to propylbenzenes and produce an effluent from the alkylation reactor containing not more than 5 vol % of fractions boiling above 225° C. and which has a T90 of not more than 230° C. and with an octane rating (RON+MON)/2 not less than 82.

16. A process according to claim 15 in which the effluent from the alkylation reactor which has a T90 of not more than 225° C.

17. A process according to claim 15 in which the reformate stream comprises from 25 to 50 weight percent benzene.

18. A process according to claim 15 in which the alkylbenzene portion of the effluent from the alkylation reactor comprises from 40-60 wt, pct, mono-propylbenzene, 30-50 wt, pct, di-isopropylbenzene and 5 to 10 wt, pct, tri-isopropyl benzene.

19. A process according to claim 15 in which the volume of the reaction effluent is at least 5 percent greater than that of the reformate feed.

20. A process according to claim 15 in which the propylene is injected at three or more points each located between catalyst beds.

21. A process according to claim 15 in which the reformate stream includes normal C5 to C8 paraffins which are isomerized during the alkylation to form non-linear paraffins of higher octane number.

22. A process according to claim 15 in which the benzene conversion is at least 90%, the propylene is injected at three or more points each located between the catalyst beds, and the alkylation product has octane numbers of at least 84 (R) and 82 (M).

23. A process according to claim 22 in which the benzene conversion is at least 90%, the propylene is injected at three or more points each located between the catalyst beds, and the alkylation product has octane numbers of at least 85 (R) and 82 (M).

24. A process according to claim 15 in which the molar ratio of the propylene-containing olefinic feed to the reformate feed is at least 2.0:1.

25. A process according to claim 24 in which the molar ratio of the propylene-containing olefinic feed to the reformate feed is from 2:1 to 3:1.

* * * * *